(12) United States Patent
Sakama et al.

(10) Patent No.: US 9,176,236 B2
(45) Date of Patent: Nov. 3, 2015

(54) DEVICE FOR MEASURING RADIATION INTENSITY OF SMALL SEALED RADIATION SOURCE FOR CANCER THERAPY

(71) Applicants: THE UNIVERSITY OF TOKUSHIMA, Tokushima (JP); LSIP, LLC, Tokyo (JP)

(72) Inventors: Minoru Sakama, Tokushima (JP); Hitoshi Ikushima, Tokushima (JP); Takaharu Yamada, Tokushima (JP); Hisashi Takai, Tokushima (JP); Teruyoshi Ichiraku, Tokushima (JP)

(73) Assignees: THE UNIVERSITY OF TOKUSHIMA, Tokushima (JP); LSIP, LLC, Tokyo (JP)

( * ) Notice: Subject to any disclaimer, the term of this patent is extended or adjusted under 35 U.S.C. 154(b) by 0 days.

(21) Appl. No.: 14/434,374

(22) PCT Filed: Oct. 2, 2013

(86) PCT No.: PCT/JP2013/005883
§ 371 (c)(1),
(2) Date: Apr. 8, 2015

(87) PCT Pub. No.: WO2014/057631
PCT Pub. Date: Apr. 17, 2014

(65) Prior Publication Data
US 2015/0241568 A1      Aug. 27, 2015

(30) Foreign Application Priority Data
Oct. 9, 2012   (JP) ................................ 2012-223836

(51) Int. Cl.
*A61N 5/10* (2006.01)
*G01T 1/161* (2006.01)

(52) U.S. Cl.
CPC .............. *G01T 1/161* (2013.01); *A61N 5/1075* (2013.01)

(58) Field of Classification Search
CPC ............................ A61N 5/1075; G01T 1/161
See application file for complete search history.

(56) References Cited

U.S. PATENT DOCUMENTS

2012/0326035 A1 * 12/2012 Saze et al. ................... 250/336.1

FOREIGN PATENT DOCUMENTS

| JP | 1-232282 A | 9/1989 |
| JP | 2006-263353 A | 5/2006 |
| JP | 2011-224030 A | 10/2011 |
| WO | 2011-067925 A1 | 6/2011 |

OTHER PUBLICATIONS

International Search Report corresponding to PCT/JP2013/005883 dated Dec. 24, 2013.

* cited by examiner

*Primary Examiner* — Mark R Gaworecki
(74) *Attorney, Agent, or Firm* — Hogan Lovells US LLP

(57) ABSTRACT

The invention provides a radiation intensity measuring apparatus for each of small sealed radiation sources for cancer therapy that is capable of measuring multiple cartridges. The apparatus includes a device for setting up multiple cartridges and a device for measuring the radiation intensities of radiation passing through a narrow slit. Radiation is emitted from multiple radiation sources and the radiation measurement device moves simultaneously together with the slit along with the side of cartridge holding device while scanning the radiation intensities. Included is a radiation detection scanning device for measuring radiation intensities for each of the radiation sources passing through the narrow slit, and a slit shielding system for restricting radiation originated originating from both the side neighboring radiation sources. The moving device is configured move the radiation measurement device along the direction in the side of cartridge where multiple radiation sources are lined up close to each other.

11 Claims, 15 Drawing Sheets

(A)          (B)

(A)

(B)

(C)

(A)

(B)

(C)

DEVICE FOR MEASURING RADIATION INTENSITY OF SMALL SEALED RADIATION SOURCE FOR CANCER THERAPY

This application is a U.S. National Phase under 35 U.S.C. §371 of International Application PCT/JP2013/005883, filed on Oct. 2, 2013, which claims priority to Japanese Patent Application No. 2012-223836 filed on Oct. 9, 2012. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention relates to a radiation intensity measuring apparatus for small sealed radiation sources for cancer therapy. More specifically, the present invention relates to a radiation intensity measuring apparatus for small sealed radiation sources for cancer therapy for measuring radiation intensity of small sealed radiation sources for use in small sealed radiation source therapy for prostate cancer.

BACKGROUND ART

The small sealed radiation source therapy for prostate cancer is principally conducted by inserting a radiation source in which [Iodine-125] which is a radioactive nuclide is hermetically sealed in a capsule made of titanium (hereinafter, simply referred to as a radiation source) into prostate. The radiation source is normally supplied in the state that 5 or 15 radiation sources are packed in a cartridge, and the cartridge C is provided in the state that it is hermetically sealed in a container in a sterile condition. The radiation sources S are packed in the cartridge C so that their axial directions are aligned (the axial directions are parallel with each other) (see FIG. 9).

In the small sealed radiation source therapy, on the assumption that the amount of radioactivity of the radioactive nuclide hermetically sealed in each radiation source is identical, the number of radiation sources to be inserted into prostate and the inserting position thereof are determined depending on the state of prostate cancer of the individual. The number of radiation sources to be inserted at one operation of the small sealed radiation source therapy is about 50 to 150.

However, it is said that the multiple radiation sources undesirably includes a defective whose amount of radioactivity is different from the nominal value of the supplier of the cartridge in the probability of about one in several hundreds of products, or about two in a hundred of products in products of bad quality. For example, a radiation source having little radioactivity, or a radiation source whose amount of radioactivity is larger than the nominal value can be included. When such a defective radiation source is used, such problems arise that an expected therapeutic effect is not obtained due to shortage of exposed dose, or conversely other tissue is influenced due to excessive exposed dose. For this reason, the American Association of Physicists in Medicine (AAPM) recommends to test at least 10%, and 100%, if possible, of the radiation sources to be used at each facility.

Originally, the radiation intensity of all the radiation sources should be measured at each facility where the radiation sources are used, however, in the method for measuring radiation intensity using an ionization chamber (radiation meter) that is generally used at present, it is necessary to measure the amount of radioactivity of the capsule one by one. Since this has the disadvantages (1) to (7) below, it is actually difficult to measure the radiation intensity of all of the radiation sources at each facility.

(1) It is necessary to take out the cartridge that is packaged in sterile condition from the bag.
(2) It is necessary to take out the radiation source from the cartridge.
(3) Since the radiation source is measured one by one, very long time is required.
(4) It is necessary to pack the radiation source taken out from the cartridge again in the cartridge.
(5) It is necessary to sterilize the cartridge into which the radiation source is packed again.
(6) It is difficult to avoid exposure to radiation of the operator's hands and fingers in the operations of (1) to (5).
(7) A special calibrated ionization chamber is required.

In this respect, a radiation intensity measuring apparatus for each radiation source in the state that the radiation source is packed in the cartridge has been developed (Patent Document 1).

Patent Document 1 discloses a technique regarding a radiation intensity measuring apparatus for a radiation source, and the measuring apparatus has a receiving part for receiving a cartridge in which small sealed radiation sources are packed in its interior, and is also provided with an insertion opening through which the cartridge is inserted into the receiving part from outside, and a plurality of openings penetrating the receiving part and outside.

With such a configuration, a cartridge is inserted into the receiving part of the measuring apparatus through the insertion opening, and the measuring apparatus is positioned on the X-ray film so that the multiple openings are in contact with the X-ray film. Since the radiation emitted from each radiation source leaks outside the measuring apparatus through the corresponding opening, the X-ray film which is in contact with the measuring apparatus is exposed to the leaking radiation, and information of the radiation intensity of each radiation source is recorded on the X-ray film. Therefore, by analyzing the record on the X-ray film, it is possible to obtain desired information.

Since the measuring apparatus of Patent Document 1 measures the radiation source packed in the cartridge as it is, the above problems (2) to (4) can possibly be cleared up, but the above problems (1) and (5) cannot be solved because measurement cannot be executed unless the cartridge packaged in a sterile condition is taken out from the bag.

In the measuring apparatus of Patent Document 1, the problem of decrease in measurement accuracy of radiation intensity arises for the reason as will be mentioned below although the above problems (2) to (4) can be solved.

In the case of the measuring apparatus of Patent Document 1, the measuring apparatus exposes the X-ray film to light by radiation respectively leaking from the multiple openings h. Therefore, for obtaining the information of the radiation intensity of each radiation source S, it is necessary to accurately align the center axes of the multiple radiation sources S and the center axes of the multiple openings h so that one radiation source corresponds to each opening h.

However, not all of the radiation sources S packed in the cartridge C are packed at the same interval, and slight difference arise in arrangement of the radiation sources S between individual cartridges C. For example, the radiation sources S can include a radiation source S having a wire diameter different from the normal wire diameter, and such a radiation source S can be packed. In this case, as illustrated in FIG. 9(C), when the positions of the multiple openings h are formed at regular intervals in accordance with a normal wire diameter of the radiation source S (0.8 mm), the center axis of a certain radiation source S can be deviated from the center axis of the opening h. As a result, a radiation source S for which accurate radiation intensity cannot be measured arises, and measurement accuracy of the radiation intensity deteriorates.

On the other hand, as a technique for solving the problems (1) to (7) of conventional methods, the technique of Patent Document 2 has been developed.

Patent Document 2 discloses a radiation intensity measuring apparatus capable of measuring radiation intensity of a radiation source packed in a cartridge to be measured in the state that the cartridge is accommodated in a bag or a container. This radiation intensity measuring apparatus has holding means for holding a cartridge accommodated in a bag or container, and an accommodating part having an accommodation space into which the cartridge held by the holding means is to be carried. The accommodating part is provided with a slit that communicates between the interior of the accommodation space and outside. For this reason, by carrying the cartridge into the accommodation space of the accommodating part by the holding means, radiation emitted from each radiation source is emitted outside the accommodating part through the slit. Therefore, by measuring the intensity of the radiation emitted outside the accommodating part, it is possible to measure the intensity of the radiation emitted from the radiation source while the cartridge is kept accommodated in a bag or container.

In addition, the slit has a width that is smaller than the axial diameter of the radiation source, so that the holding means can carry the cartridge into the accommodation space while keeping the axial direction of the slit and the axial directions of the radiation sources packed in the cartridge parallel with each other. Therefore, as the radiation sources packed in the cartridge are sequentially passed through the position of the slit, the intensity of radiation emitted outside the accommodating part through the slit varies with movement of the radiation sources. Therefore, by measuring the variation in radiation intensity, it is possible to calculate the intensity of radiation emitted from each radiation source based on the variation in the radiation intensity.

PRIOR ART DOCUMENTS

Patent Documents

Patent Document 1: Japanese Utility Model Registration No. 3132529
Patent Document 2: WO 2011-067925 A

SUMMARY OF THE INVENTION

Problems to be Solved by the Invention

As described above, by using the radiation intensity measuring apparatus of Patent Document 2, it is possible to measure the radiation intensity of a radiation source while keeping the cartridge hermetically sealed in a bag or a container, however, in the apparatus of Patent Document 2, the operator has to make the cartridge held by the holding means one by one. In other words, in the radiation intensity measuring apparatus of Patent Document 2, the holding means cannot hold multiple cartridges at once. Therefore, in measuring multiple cartridges, the operator need to repeat the operation of detaching the cartridge for which measurement has completed from the holding means, and supplying the holding means with a new cartridge. Therefore, time and labor are required, and the operation time extends.

In the radiation intensity measuring apparatus of Patent Document 2, the holding means has to hold the radiation source held by the cartridge in a predetermined posture (the state that the axial direction of the radiation source is parallel with the axial direction of the slit). As a result, in measuring the radiation intensity of the radiation source S for radiation sources held by a container or cartridge having different shape, the holding means adapted to the shape of the container or cartridge is required. For measuring radiation intensity of a radiation source held by a container or cartridge having a different shape, it is necessary to change the holding means. In the radiation intensity measuring apparatus of Patent Document 2, since the holding means is configured to carry the cartridge into the accommodation space of the accommodating part, time and labor are required for changing operation of the holding means. Therefore, in the radiation intensity measuring apparatus of Patent Document 2, it is difficult to rapidly correspond to the change in cartridge to be measured.

Further, in the radiation intensity measuring apparatus of Patent Document 2, the holding means that holds the cartridge is moved. Since the cartridge has a certain degree of size, the holding means inevitably has a certain degree of size. Accordingly, the size of the mechanism for moving the holding means increases, and it is difficult to downsize the apparatus.

In light of the above circumstances, it is an object of the present invention to provide a radiation intensity measuring apparatus for small sealed radiation sources for cancer therapy capable of measuring multiple cartridges efficiently as well as quickly, and capable of downsizing the apparatus.

Means for Solving the Problems

A radiation intensity measuring apparatus for small sealed radiation sources for cancer therapy according to the first aspect of the invention is a radiation intensity measuring apparatus for multiple radiation sources, in which multiple radiation sources are held in a cartridge, and radiation intensity of the multiple radiation sources is measured while they are held by the cartridge, the apparatus includes: holding means capable of holding the cartridge; radiation intensity measuring means for measuring intensity of radiation emitted from the multiple radiation sources packed in the cartridge in the state that the cartridge is held by the holding means; and moving means for moving the radiation intensity measuring means toward or away from the holding means, the holding means includes: a radiation emitting part capable of emitting radiation emitted from the multiple radiation sources outside the holding means in the state that the cartridge is held by the holding means, the radiation intensity measuring means includes: a sensor for measuring radiation intensity, and a shielding member provided for restricting radiation irradiated to the sensor; the shielding member is disposed to be positioned between the radiation emitting part of the holding means and the sensor in a measurement state where the radiation intensity measuring means is moved toward the radiation emitting part of the holding means, the shielding member is formed with a slit that penetrates between a face positioned on the side of the radiation emitting part of the holding means and a face positioned on the side of the sensor in the measurement state, the slit is formed so that width thereof is smaller than a wire diameter of the radiation source, the moving means is configured to be able to relatively move the radiation intensity measuring means along the direction orthogonal to an axial direction of each radiation source held by the cartridge in the measurement state.

The radiation intensity measuring apparatus for small sealed radiation sources for cancer therapy according to the second aspect of the invention is characterized in that the moving means is controlled to move the radiation intensity measuring means also in an axial direction of the radiation source in relatively moving the radiation intensity measuring means along the direction orthogonal to the axial direction of the radiation source held by the cartridge in the measurement state in the first aspect of the invention.

The radiation intensity measuring apparatus for small sealed radiation sources for cancer therapy according to the third aspect of the invention is characterized in that the cartridge has a seed holding part in which the multiple radiation sources are packed so that the axial directions of the plural radiation sources are substantially parallel with each other, and the moving means is configured to be able to relatively move the radiation intensity measuring means along the direction in which the multiple radiation sources are arranged in the seed holding part of the cartridge in the measurement state in the first or second aspect of the invention.

The radiation intensity measuring apparatus for small sealed radiation sources for cancer therapy according to the fourth aspect of the invention is characterized in that the holding means is configured to be able to hold multiple cartridges, and has a plurality of radiation emitting parts respectively corresponding to positions of the seed holding parts of the multiple cartridges in the state that the multiple cartridges are held in the first, second or third aspect of the invention.

The radiation intensity measuring apparatus for small sealed radiation sources for cancer therapy according to the fifth aspect of the invention is characterized in that the moving means is able to position the radiation intensity measuring means to give a state that an axial direction of the radiation source to be measured in the measurement state and an axial direction of the slit of the shielding member are parallel with each other, and move the radiation intensity measuring means while keeping the state in the first, second, third or fourth aspect of the invention.

The radiation intensity measuring apparatus for small sealed radiation sources for cancer therapy according to the sixth aspect of the invention is characterized in that the holding means has an opposed face situated on the side of the radiation intensity measuring means in the measurement state, and a supply face situated on the opposite side of the opposed face, the supply face is formed with an accommodation groove recessed from the supply face to the opposed face, for accommodating the cartridge, the accommodation groove is formed so that the axial directions of the multiple radiation sources are parallel with the opposed face when the cartridge is accommodated in the accommodation groove, and the radiation emitting part is formed at positions corresponding to the positions where the multiple radiation sources are positioned when the cartridge is accommodated in the accommodation groove in any one of the first to fifth aspects of the invention.

The radiation intensity measuring apparatus for small sealed radiation sources for cancer therapy according to the seventh aspect of the invention is characterized in that the radiation emitting part is a through hole penetrating between an inner bottom face of the accommodation groove and the opposed face in the sixth aspect of the invention.

The radiation intensity measuring apparatus for small sealed radiation sources for cancer therapy according to the eighth aspect of the invention is characterized in that the apparatus further includes a base in which the moving means is provided, and the holding means includes: a holding plate for holding the cartridge, and a frame part for positioning the holding plate apart from the base, the radiation emitting part is provided at a position where radiation from the radiation source can be emitted into a space between the holding plate and the base in the holding plate, and the radiation intensity measuring means is disposed to be able to move in the space between the holding plate and the base by the moving means in any one of the first to seventh aspects of the invention.

The radiation intensity measuring apparatus for small sealed radiation sources for cancer therapy according to the ninth aspect of the invention is characterized in that the holding plate has a flat reference face on the side of the base, and holds the cartridge so that the axial directions of the multiple radiation sources are parallel with the reference face, the radiation intensity measuring means is provided so that a shielding face situated on the side of the radiation emitting part of the holding means in the shielding member and the reference face are parallel with each other, and the moving means moves the radiation intensity measuring means while keeping the shielding face and the reference face parallel with each other in the eighth aspect of the invention.

The radiation intensity measuring apparatus for small sealed radiation sources for cancer therapy according to the tenth aspect of the invention is characterized in that the holding plate is provided detachably from the frame part in the eighth or ninth aspect of the invention.

The radiation intensity measuring apparatus for small sealed radiation sources for cancer therapy according to the eleventh aspect of the invention is characterized in that the apparatus further includes a calibration part provided with a reference radiation source which is a reference of intensity of radiation emitted from the radiation source, and the shielding member is movable between a measurement position where a detecting part of the sensor is covered, and a calibration position where the detecting part of the sensor is exposed, and the calibration part is provided with a shielding member moving mechanism for moving the shielding member to the calibration position while moving the radiation intensity measuring means to the position of the reference radiation source of the calibration part by the moving means in any one of the first to tenth aspect of the invention.

Effect of the Invention

According to the first aspect of the invention, by making the holding means hold the cartridge, and moving the radiation intensity measuring means toward or away from the holding means by the moving means, it is possible to measure the intensity of the radiation emitted from the radiation emitting parts by the sensor of the radiation intensity measuring means. In addition, in the measurement state, the shielding member having the slit is disposed between the radiation emitting part and the sensor. Therefore, by relatively moving the radiation intensity measuring means along the direction orthogonal to the axial direction of the radiation source by the moving means, it is possible to measure the intensity of the radiation emitted from the radiation source as a variation in the radiation intensity.

According to the second aspect of the invention, by moving the radiation intensity measuring means also in the axial direction of the radiation source, it is possible to measure the radiation intensity of the radiation source based on the measurement result at the position where the radiation intensity can be measured maximally in the axial direction of the radiation source. Therefore, it is possible to improve the estimation accuracy of the intensity of the radiation of the radiation source.

According to the third aspect of the invention, by moving the radiation intensity measuring means along the direction in which the multiple radiation sources are arranged, it is possible to sequentially measure the radiation intensity of the multiple radiation sources. Therefore, it is possible to reduce the time required for measuring the radiation intensity of the multiple radiation sources.

According to the fourth aspect of the invention, since the holding means holds the multiple cartridges, it is possible to sequentially measure the radiation intensity of the radiation sources packed in the multiple cartridges merely by moving the radiation intensity measuring means by the moving means. As a result, it is not necessary to replace the measured cartridge by the cartridge to be measured next every time each cartridge is measured, so that it is possible to reduce the operation time for the operation of measuring the radiation intensity of the radiation sources packed in the multiple cartridges.

According to the fifth aspect of the invention, since the radiation intensity measuring means is moved by the moving means while the axial directions of the multiple radiation sources are kept parallel with the axial direction of the slit of the shielding member, it is possible to accurately measure the intensity of the radiation emitted from each radiation source.

According to the sixth aspect of the invention, only by accommodating the cartridge in the accommodation groove, the multiple radiation sources are positioned so that their axial directions are parallel with the opposed face. As a result, it is not necessary to conduct the operation of registering the axial directions of the radiation sources to the opposed face by adjusting the posture of the cartridge in accommodating the cartridge in the accommodation groove, so that it is possible to reduce the preparation time for measuring the radiation intensity. Since it is only required to accommodate the cartridge in the accommodation groove, the time during which the operator touches the cartridge is reduced, and hence the exposed dose of the operator also can be reduced.

According to the seventh aspect of the invention, since the radiation emitting part is a through hole, it is possible to simplify the structure of the holding means. In addition, since attenuation of radiation between the multiple radiation sources and the sensor can be reduced, it is possible to accurately grasp the intensity of the radiation emitted from the radiation source.

According to the eighth aspect of the invention, since radiation is emitted from the radiation source into the space between the holding plate and the base, it is possible to reduce the amount of radiation leaking outside from the apparatus.

According to the ninth aspect of the invention, it is possible to make the positional relation between the radiation source in the seed holding part of the multiple cartridges held by the holding plate, and the sensor of the radiation intensity measuring means substantially identical in any cartridge. As a result, it is possible to prevent occurrence of difference in measuring result of radiation intensity between different cartridges.

According to the tenth aspect of the invention, since the holding plate is provided detachably from the main body, it becomes possible to measure a cartridge of different shape only by changing the holding plate. Therefore, it is possible to readily change the cartridge to be measured. In addition, if the cartridge is provided in the state of being accommodated in the holding plate, there is no need to set the cartridge in the holding plate. As a result, preparation for measurement of radiation intensity can be conducted in short time, and the operator hardly needs to touch the cartridge, and thus the exposed dose of the operator can be further reduced.

According to the eleventh aspect of the invention, by moving the radiation intensity measuring means to the position of the reference radiation source of the calibration part by the moving means, it is possible to conduct calibration of the sensor automatically. In addition, by conducting calibration of the sensor every time before measuring each cartridge, it is possible to keep the accuracy of estimating the radioactivity of the radiation source of each cartridge high.

BRIEF DESCRIPTION OF THE DRAWINGS

FIG. 7(A) is a section view in the x direction of FIG. 1, and FIG. 7(B) is a section view in the y direction of FIG. 1.

FIG. 8 are explanatory views of a holding plate 12 alone, in which FIG. 8(A) is a plan view, and FIG. 8(B) is a section view along the line B-B.

FIG. 10 are schematic explanatory views of a plastic case PK accommodating the cartridge C, in which FIG. 10(A) is a lateral view, FIG. 10(B) is a plan view, and FIG. 10(C) is a view taken in the direction of the arrow C in FIG. 10(A).

FIG. 11 are schematic explanatory views of a rectangular cartridge C2, in which FIG. 11(A) is a perspective view, FIG. 11(B) is a plan view, and FIG. 11(C) is a lateral view.

FIG. 12 are schematic explanatory views of a holding plate 12B for the rectangular cartridge C2, in which FIG. 12(A) is a plan view in the state that the rectangular cartridge C2 is accommodated, FIG. 12(B) is a plan view of the holding plate 12B alone, and FIG. 12(C) is a back side view of the holding plate 12B alone.

FIG. 13 are schematic explanatory views of a shaft-shaped cartridge C3, in which FIG. 13(A) is a perspective view, FIG. 13(B) is a lateral view, and FIG. 13(C) is a plan view.

FIG. 14 are schematic explanatory views of a holding plate 12C for the shaft-shaped cartridge C3, in which FIG. 14(A) is a plan view in the state that the shaft-shaped cartridge C3 is accommodated, FIG. 14(B) is a plan view of the holding plate 12C alone, and FIG. 14(C) is a back side view of the holding plate 12C alone.

MODE FOR CARRYING OUT THE INVENTION

Next, embodiments of the present invention will be described with reference to the attached drawings.

A radiation intensity measuring apparatus for small sealed radiation sources for cancer therapy is used for measuring an amount of radioactivity of a radioactive nuclide hermetically sealed in a radiation source for use in a small sealed radiation source therapy for prostate cancer, and is able to measure the intensity of the radiation emitted from the radiation sources packed in the cartridge.

(Description of Radiation Source S and Cartridge C)

As described above, the radiation intensity measuring apparatus for small sealed radiation sources for cancer therapy according to the present embodiment (hereinafter, referred to as a radiation intensity measuring apparatus 1 of the present embodiment) measures the intensity of the radiation emitted from radiation sources S packed in the cartridge. Before describing the radiation intensity measuring apparatus, the radiation sources S which are objects to be measured, and the cartridge C in which the radiation sources S are packed will be described.

(Regarding Radiation Source S)

The radiation source S is prepared by hermetically sealing [Iodine-125] which is a radioactive nuclide in a capsule made of titanium, and has such a shape that the axial length is longer than the wire diameter. The radiation source S that is commonly used has a wire diameter ranging from 0.80 to 0.95 mm and an axial length ranging from 4.50 to 4.55 mm, and the wire diameter and the axial length have slight variations.

(Regarding Cartridge C)

Next, the cartridge C that holds the radiation sources S will be described.

Figure 11:
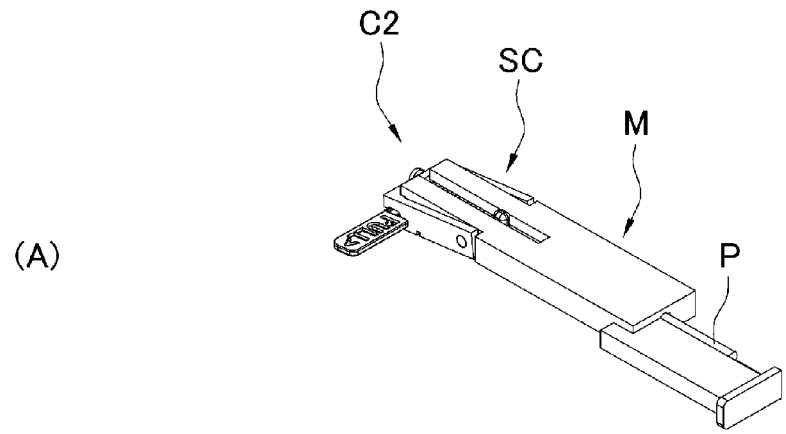
Figure 11:
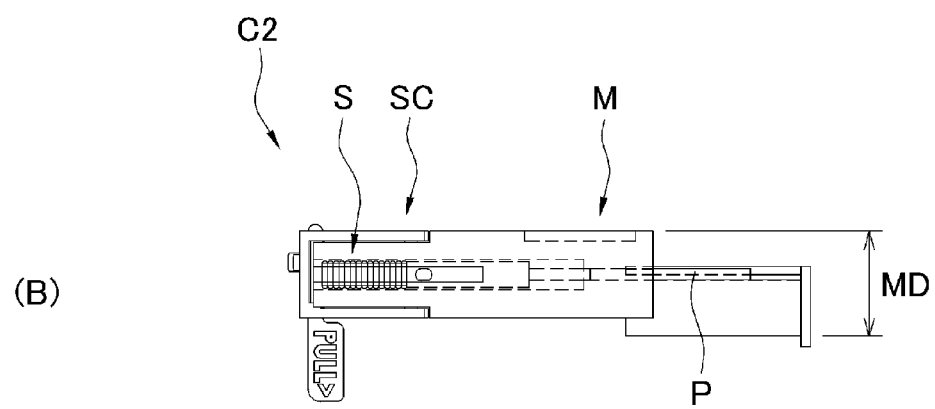
Figure 11:
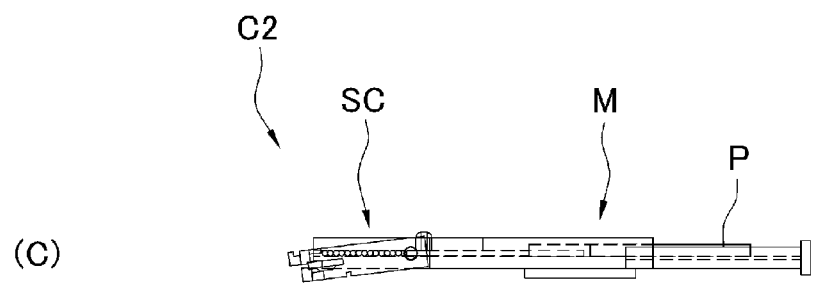
Figure 13:
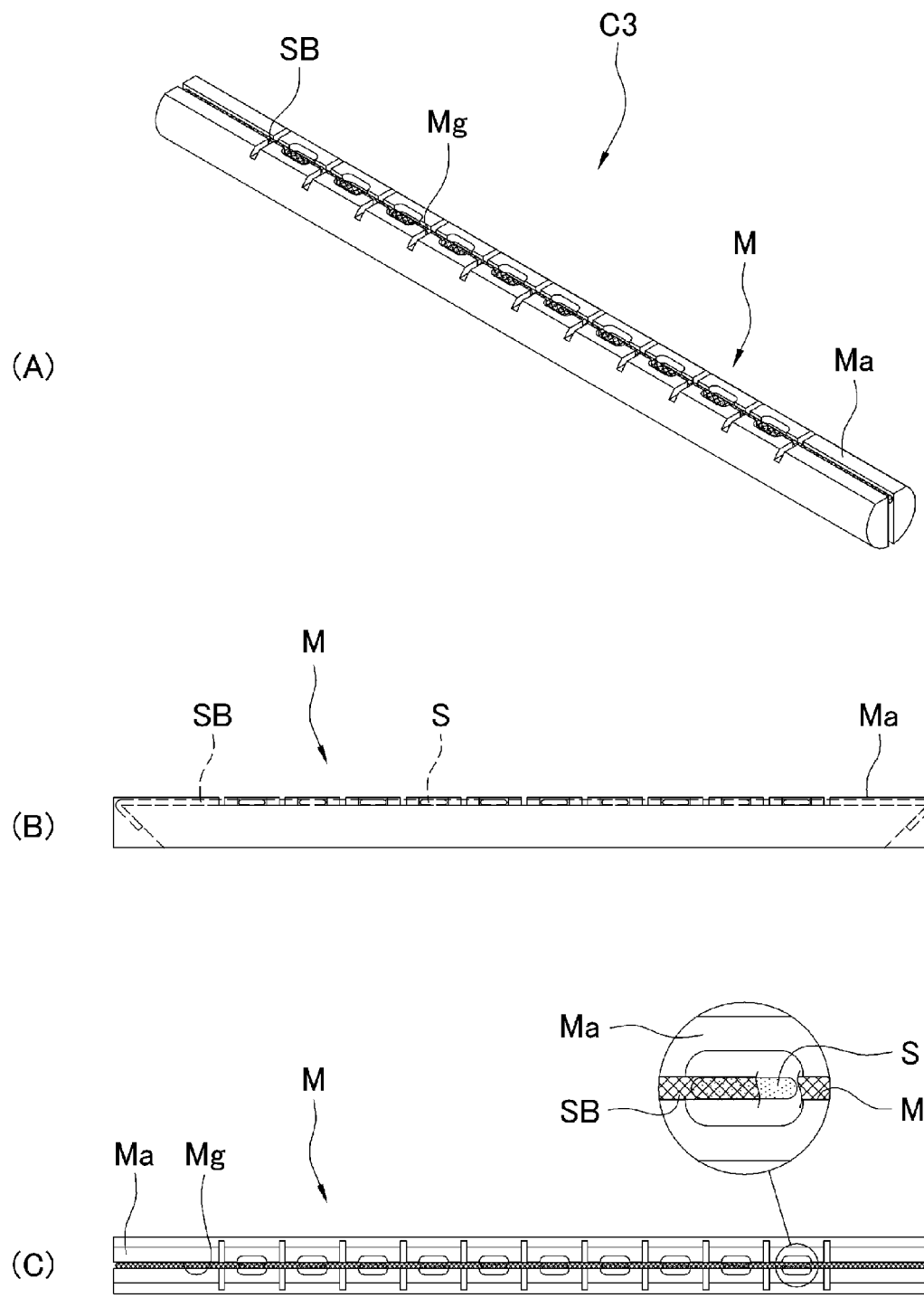

The cartridge C is generally used for small sealed radiation source therapy for prostate cancer, and normally used in the state that it holds multiple radiation sources S. As the shape of the cartridge C, various shapes are used. For example, the one having a shape as illustrated in FIG. 9(A), the one having a shape as illustrated in FIG. 11, and the one having a shape as illustrated in FIG. 13 are used, however, the cartridge C for measuring the radiation intensity of the radiation sources S in the radiation intensity measuring apparatus 1 of the present embodiment is not particularly limited.

Figure 9:
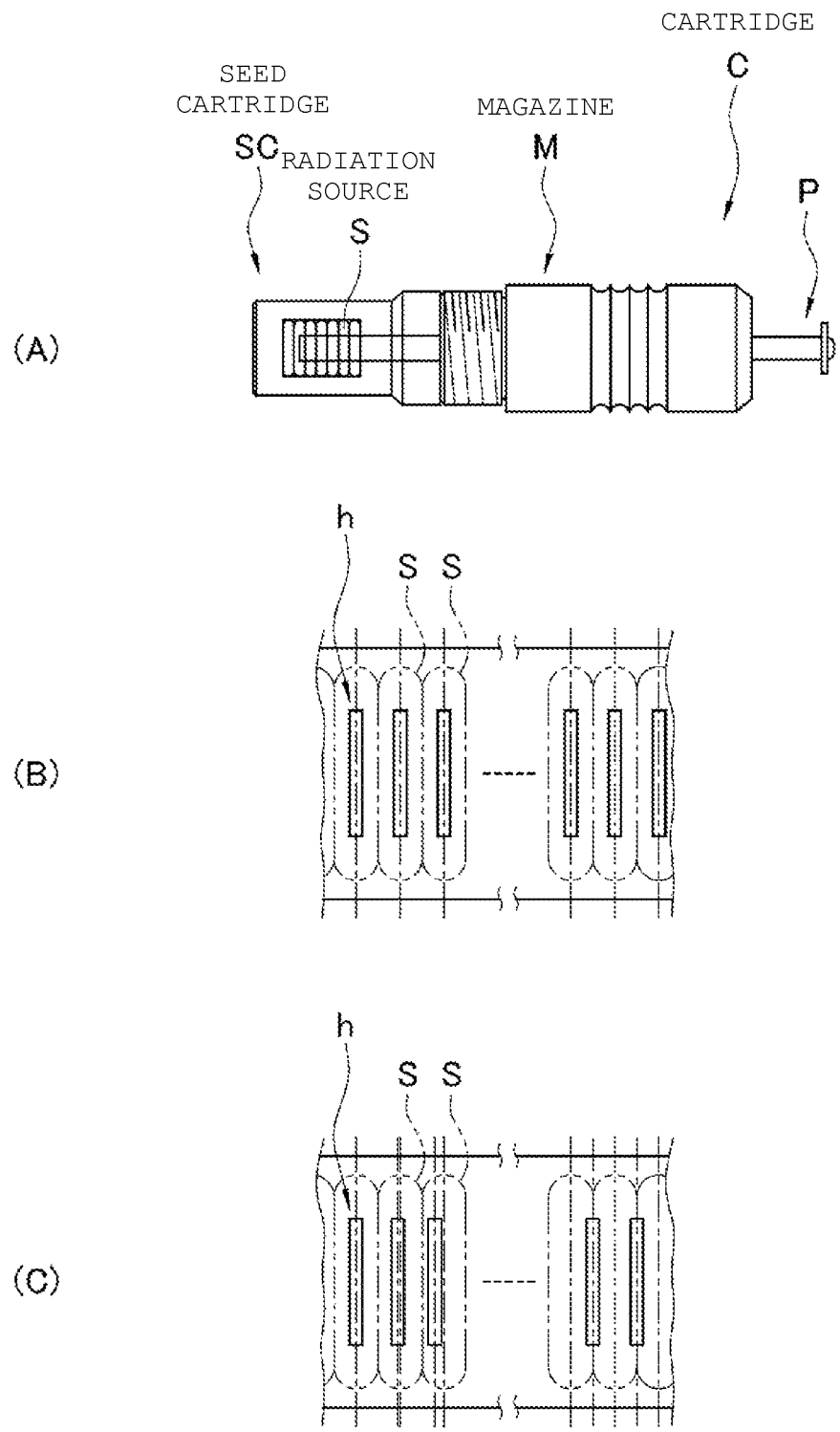
FIG. 9(A) is a schematic explanatory view of a cartridge C.
FIGS. 9(B) and 9(C) are schematic explanatory views of a slit h part in the state that cartridge C is inserted into a measuring apparatus of Patent Document 1.

First, the cartridge C having the shape as illustrated in FIG. 9(A) will be described.

As illustrated in FIG. 9(A), the cartridge C includes a magazine M having a substantially cylindrical shape, a seed cartridge SC in which multiple radiation sources S are packed, provided at one of axial ends of the magazine M, and a pusher P in the form of a rod penetrating the center axis of the magazine M. A tip end of the pusher P reaches the space where the radiation sources S are packed in the seed cartridge SC, and has a function of holding the multiple radiation sources S packed in the seed cartridge SC in the state that they are in close contact with each other with the axial directions thereof being parallel with each other.

The aforementioned seed cartridge SC is located on the center axis of the magazine M. The seed cartridge SC is a plate-like member (about 3.1 mm in thickness) having a tip end face formed into a flat plane orthogonal to the center axis of the magazine M, and a surface formed into a plane parallel with the center axis of the magazine M. The seed cartridge SC has the aforementioned space in which the radiation source S is packed. This space is formed so that the height of its section is substantially the same with the wire diameter of the radiation source S, and the width of its section is substantially the same with the length of the radiation source S. The space is formed in such a manner that the axial directions of the multiple radiation sources S are parallel with the tip end face and the surface of the seed cartridge SC, when the multiple radiation sources S are held by the aforementioned pusher P in such a state that they are in close contact with each other and their axial directions are parallel with each other.

The number of radiation sources S packed in the space of the seed cartridge SC is not particularly limited, but it is generally five or fifteen.

Regarding "magazine M having a substantially cylindrical shape" used in the above description, a substantially cylindrical shape is conceptual wording including the shapes such as a hexagon or an octagon generally employed in a magazine M of a cartridge C.

(Regarding Other Cartridge)

Next, the cartridge having the shape illustrated in FIG. 11 (rectangular cartridge C2) will be described.

Figure 12:
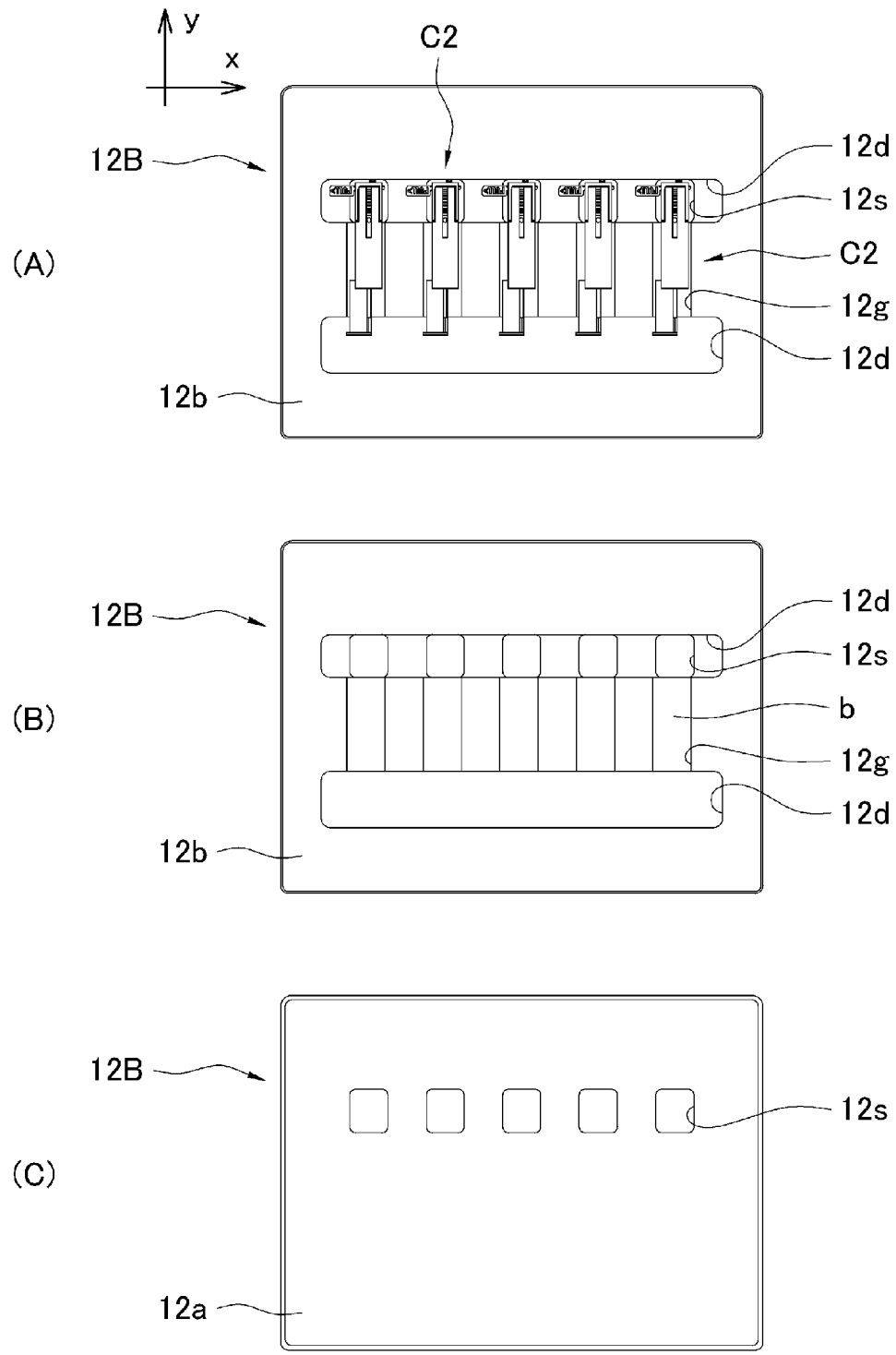

As illustrated in FIG. 12, the rectangular cartridge C2 has a substantially rectangular main body M whose opposing surfaces are formed into flat planes that are parallel with each other. The main body M has a hollow space capable of accommodating the radiation sources S therein, and one of its end parts (left end in FIGS. 12(B) and 12(C)) forms the seed cartridge SC in which the multiple radiation sources S are packed.

The main body M of the rectangular cartridge C2 is provided with the pusher P having the same function as the aforementioned cartridge C (see FIG. 9(A)). The pusher P is a rod-like member that penetrates the center axis of the main body M, and is provided to be able to push the multiple radiation sources S in the main body M toward one of the end parts of the main body M.

In the main body M of the rectangular cartridge C2, the internal space of the seed cartridge SC is formed so that the height of the section is substantially identical to the wire diameter of the radiation source S, and the width of the section is substantially identical to the length of the radiation source S. The inner surface of the interior of the seed cartridge SC is formed to be substantially parallel with the surface of the seed cartridge SC (in other words, the surface of the main body M).

The multiple radiation sources S are accommodated in the internal space of the main body M of the rectangular cartridge C2, and the multiple radiation sources S are pushed by the aforementioned pusher P. As a result, the multiple radiation sources S are held in the seed cartridge SC in the state that their axial directions are parallel with each other and they are in close contact with each other. Also, the multiple radiation sources S are packed in the seed cartridge SC in such a manner that their axial directions are parallel with the surface of the seed cartridge SC.

Also in the rectangular cartridge C2, the number of radiation sources S packed in the space of the seed cartridge SC is not particularly limited, but it is generally five or fifteen as is the case with the cartridge C.

(Regarding Still Another Cartridge)

Next, the cartridge having the shape illustrated in FIG. 13 (shaft-shaped cartridge C3) will be described.

As illustrated in FIG. 13, unlike the cartridge C and the rectangular cartridge C2 as described above, the shaft-shaped cartridge C3 holds a pair of radiation sources S while connecting them so that their axial directions are substantially coaxial.

In the shaft-shaped cartridge C3, its main body M is formed into a substantially cylindrical shape. The shaft-shaped cartridge C3 is formed with a flat plane Ma that is parallel with the axial direction of the main body M, on the side face of the main body M. The flat plane Ma is formed with a groove Mg along the axial direction of the main body M, and in the groove Mg, a strap member SB accommodating the radiation sources S therein is accommodated. The strap member SB accommodates the radiation sources S at constant intervals along its axial direction. And, the radiation sources S are arranged so that their axial directions coincide with the axial direction of the strap member SB.

In the shaft-shaped cartridge C3 having the structure as described above, by disposing the strap member SB in the groove Mg of the main body M, it is possible to hold the radiation sources S in the state that they are arranged along the axial direction of the main body M at constant intervals.

Preferably, the strap member SB is formed to have a thickness that will not fall out of the groove Mg when it is arranged in the groove Mg with the radiation sources S accommodated therein. The configuration of fixing the strap member SB in the groove Mg, or in other words, the configuration of preventing the strap member SB from falling out of the groove Mg is not particularly limited. For example, from the view point of preventing the strap member SB from falling out of the groove Mg, a structure that allows hooking of both end parts of the strap member SB may be provided in end parts of the groove Mg of the main body M. Concretely, a projection or the like may be provided in end parts of the groove Mg of the main body M to fix the strap member SB in the groove Mg. In particular, by forming end parts in the groove Mg to have an acute angle, it is possible to make the strap member SB difficult to fall out of the groove Mg (see FIG. 13).

(Regarding a Further Other Cartridge)

Also the one connecting a pair of radiation sources S so that their axial directions are substantially coaxial, and retaining the same may be used as a cartridge.

For example, as the cartridge, a substantially cylindrical cartridge having an insertion hole through which the radiation source S is inserted in both end parts (or in either end part) is used. In this case, the insertion hole is formed so that its inner diameter is slightly smaller than the diameter of the radiation source S. That is, the insertion hole of the cartridge is formed to have a size capable of holding the radiation source S so that the radiation source Swill not fall off when the radiation source S is inserted into the insertion hole.

As a result, by attaching the multiple radiation sources S to the insertion hole of the cartridge, it is possible to connect the multiple radiation sources S via the cartridge.

The number of radiation sources S connected by the cartridge (connecting cartridge) is not particularly limited. Since the cartridge having such a structure is normally placed in a living body together with the radiation sources S, an appropriate number of radiation sources S may be connected depending on, for example, the place where the radiation sources S are placed together with the cartridge.

(Regarding Package of Cartridge C)

The cartridge C, the rectangular cartridge C2, the shaft-shaped cartridge C3, the connecting cartridge and so on described above (hereinafter, simply referred to as cartridge C) can be provided while the multiple cartridges C are packaged in a container such as a can in hermetically sealed and sterilized condition. In this case, the cartridge C is taken out from the container, and the cartridge C is held in the holding means as will be described later, and the radiation intensity of the radiation sources S packed in the cartridge C is measured.

On the other hand, the cartridge C can be provided while it is individually packaged in a bag or container in hermetically sealed and sterilized condition. For example, the cartridge C may be provided while it is hermetically sealed in a bag made up of a paper sheet (backing paper) of about 0.18 mm in thickness, and a synthetic resin sheet (cover sheet) of about 0.05 mm in thickness. Concretely, the peripheral parts of the sheets are bonded together with the cartridge C sandwiched therebetween to hermetically seal the cartridge C in the bag, and thus the cartridge C that is hermetically sealed in the bag can be provided.

In the case where the cartridge C is provided while it is hermetically sealed in a bag or a container individually, the cartridge C may be taken out from the bag or the container and the radiation intensity of the radiation sources S may be measured in the same manner as in the case where the multiple cartridges C are provided while they are hermetically sealed in the container in sterilized condition. However, in the case where the cartridge C is provided while it is hermetically sealed in a bag or a container individually, it is possible to measure the radiation intensity of the radiation source S while keeping the cartridge C hermetically sealed in the bag or the container. As will be described later, by making the shape of the holding means (accommodation groove 12g of holding plate 12) coincident with the shape of the bag or the container, it is possible to measure the cartridge C while keeping it hermetically sealed in the bag or the container.

For example, when the cartridge C has the shape as illustrated in FIG. 9(A), it becomes possible to measure the radiation intensity of the radiation sources S while keeping the cartridge C accommodated in the container by the radiation intensity measuring apparatus 1 of the present invention by employing the following shape.

Figure 10:
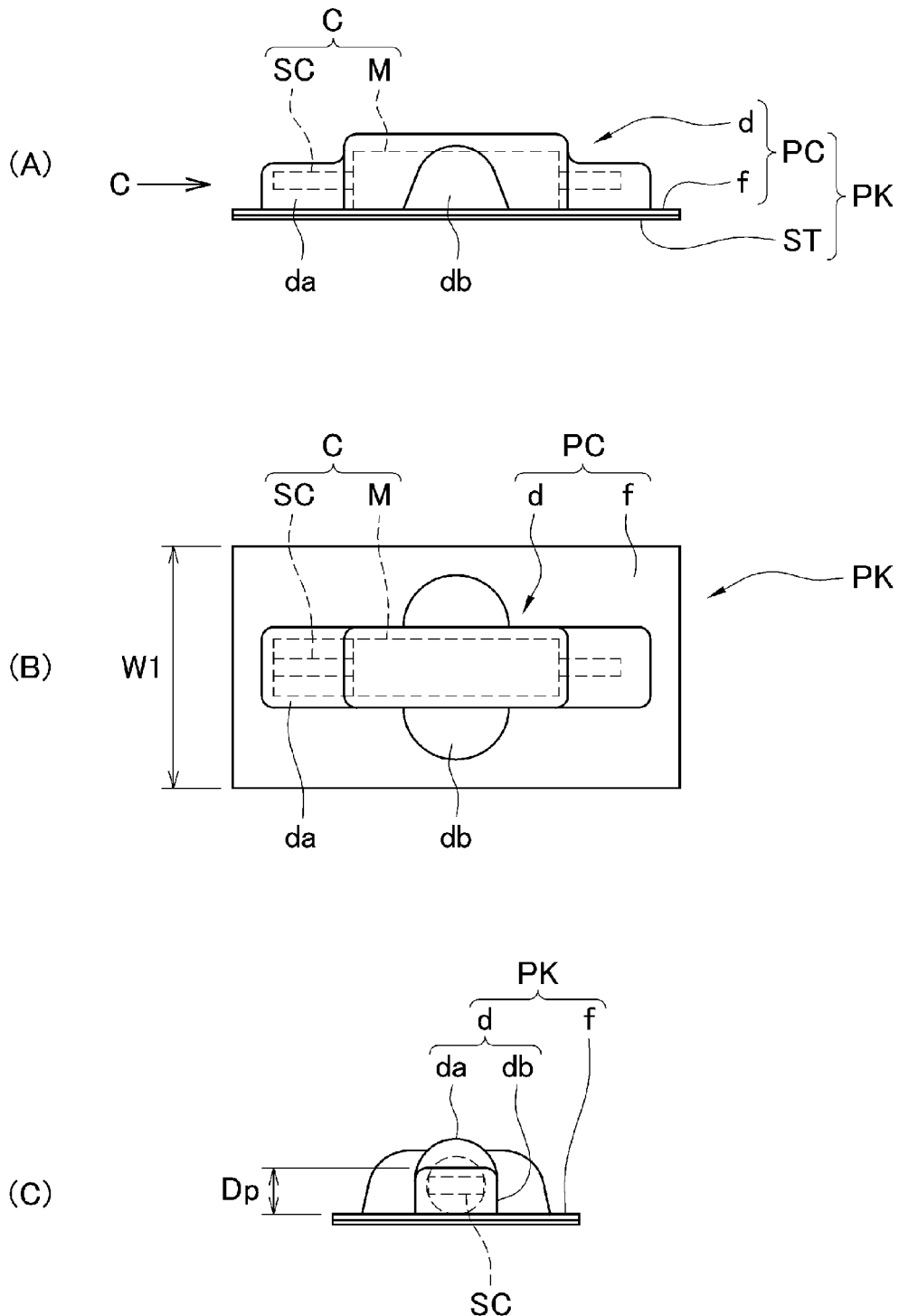

In FIG. 10, the reference symbol PK denotes a plastic case that accommodates the cartridge C.

As shown in FIG. 10, the plastic case PK is made up of a plastic accommodation case PC having a recessed part (hereinafter, referred to as a recess part d), and a cover sheet ST provided to close the opening of the recess part of the accommodation case PC.

As shown in FIG. 10, the accommodation case PC is a member formed of a plastic material having a certain degree of strength. The accommodation case PC includes the recess part d accommodating the cartridge C therein, and a flange part f provided in the periphery of the opening of the recess part d.

The recess part d is so formed that when the cartridge C is accommodated therein, the axial direction of the cartridge C substantially coincides with the axial direction of the recess part d, and motion of the cartridge C inside the same can be limited.

Concretely, in the center part of the recess part d, a magazine accommodating part db for accommodating the magazine M of the cartridge C is provided. The magazine accommodating part db has a depth and a width that are slightly larger than the diameter of the magazine M, and has a length that is slightly larger than the axial length of the magazine M.

The magazine accommodating part db has a shape capable of holding the magazine M so that the axial direction of the magazine M accommodated therein substantially coincides with the axial direction of the magazine accommodating part db.

On the lateral side of the magazine accommodating part db, a seed cartridge accommodating part da which is a space communicating with the magazine accommodating part db is provided. The seed cartridge accommodating part da is formed to accommodate the seed cartridge SC when the magazine M of the cartridge C is accommodated in the magazine accommodating part db.

The seed cartridge accommodating part da is formed so that when the seed cartridge SC is accommodated therein, the axial direction of the seed cartridge accommodating part da and the axial directions of the multiple radiation sources S in the seed cartridge SC are substantially orthogonal to each other.

The seed cartridge accommodating part da is formed so that the bottom of its recess (top face in FIG. 10) is a flat plane, and has a depth Dp that is roughly equivalent to the sum of the radius of the magazine M and the thickness of the seed cartridge SC.

The width of the seed cartridge accommodating part da is slightly wider than the width of the seed cartridge SC. Concretely, it is formed to be wider than the width of the seed cartridge SC by about several millimeters.

The recess part d also has a recess substantially identical to the seed cartridge accommodating part da on the opposite side of the seed cartridge accommodating part da with respect to the magazine accommodating part db.

The flange part f is provided on the periphery of the opening of the recess part d, and has the surface (top face and bottom face in FIG. 10) parallel with the bottom face of the seed cartridge accommodating part da.

Since the recess part d and the flange part f are formed in the manner as described above, when the cartridge C is accommodated in the recess part d of the accommodation case PC, the axial direction of the cartridge C substantially coincides with the axial direction of the recess part d. In addition, the cartridge C is positioned so that the surface of the seed cartridge SC is substantially parallel with the bottom face of the seed cartridge accommodating part da or the surface of the flange part f.

In this state, the cover sheet ST is arranged to cover the opening of the recess part d to make the cover sheet ST and the flange part f adhere airtightly, and thus the cartridge C can be hermetically sealed in the plastic case PK.

In addition, by bonding the cover sheet ST on the flange part f of the accommodation case PC, the cartridge C is restricted from moving in its axial direction. This is because when the cartridge C is about to move in the axial direction, the axial end face of the magazine M comes into contact with the wall face that connects the magazine accommodating part db and the seed cartridge accommodating part da and so on, and can no longer move.

When the cover sheet ST is bonded on the flange part f of the accommodation case PC, the cartridge C is restricted from rotating about its axis. This is because the surface of the seed cartridge SC is in surface contact with the bottom face of the seed cartridge accommodating part da, or there is only a small gap between these.

Therefore, the cartridge C being accommodated in the plastic case PK is held in the state that the axial direction of the cartridge C substantially coincides with the axial direction of the recess part d (namely, axial direction of the container PK), and the surface of the seed cartridge SC is almost parallel with the surface of the flange part f (top face in FIG. 10).

(Description of Radiation Intensity Measuring Apparatus 1 of the Present Embodiment)

Next, the radiation intensity measuring apparatus 1 of the present embodiment will be described. Before describing the details of each part of the apparatus, the structure of the apparatus and the operation thereof will be briefly described.

In FIG. 1 to FIG. 4, the reference numeral 2 denotes a base of the radiation intensity measuring apparatus 1.

On the top face of the base 2, a holding means 10 is provided. The holding means 10 has a holding plate 12 distanced from the top face of the base 2. The holding plate 12 can accommodate multiple cartridges C in which radiation sources S for measuring the radiation intensity are packed, or multiple containers PK accommodating cartridges C. The holding plate 12 is formed with a radiation emitting part 12s to make the radiation emitted from the radiation sources S of the accommodated cartridges C to be emitted in the space between the top face of the base 2 and the holding plate 12 (see FIG. 3, hereinafter, referred to as a measurement space 1h) (see FIG. 8).

On the other hand, in the measurement space 1h, a moving means 20 and a radiation intensity measuring means 30 are disposed.

The radiation intensity measuring means 30 measures the intensity of the radiation emitted from the radiation source S of the cartridge C.

The moving means 20 moves the radiation intensity measuring means 30 in the measurement space 1h. Concretely, the moving means 20 has a function of moving the radiation intensity measuring means 30 toward or away from the multiple cartridges C accommodated in the holding plate 12.

Since the configuration as described above is employed, by accommodating multiple cartridges C each packed with the radiation sources S for which the radiation intensity is to be measured, in the holding plate 12, and sequentially moving the radiation intensity measuring means 30 toward the multiple cartridges C accommodated in the holding plate 12 by the moving means 20, it is possible to sequentially measure the radiation intensity of the radiation sources S packed in the multiple cartridges C. That is, it is possible to successively measure the radiation intensity of the radiation sources S packed in the multiple cartridges C.

As a result, it is no longer necessary to replace the measured cartridge C with the cartridge C to be measured next every time the radiation intensity of the radiation sources S packed in each cartridge C is measured. Therefore, it is possible to reduce the operation time required for measuring the radiation intensity of the radiation sources S packed in the multiple cartridges C.

Of course, the holding plate 12 may be structured to accommodate only one cartridge C or container PK accommodating the cartridge C. As descried above, by employing the structure capable of accommodating multiple cartridges C and so on, it is possible to obtain the merit of avoiding the necessity of replacing the measured cartridge C with the cartridge C to be measured next every time. On the other hand, by employing the structure capable of accommodating only one cartridge C in the holding plate 12, it is possible to obtain the merit of downsizing the holding plate 12, and thus downsizing the apparatus itself.

In the following, each part of the radiation intensity measuring apparatus 1 according to the present embodiment will be described in detail.

(Base 2)

In FIG. 1 to FIG. 4, the reference numeral 2 denotes a base of the radiation intensity measuring apparatus 1. The base 2 is formed, for example, of a plate-like member, however, the method for forming the base 2 is not particularly limited.

(Frame Part 11)

As shown in FIG. 1 to FIG. 4, on the top face of the base 2, the holding means 10 is provided. The holding means 10 has a frame part 11 and the holding plate 12.

The frame part 11 is provided for holding the holding plate 12 in the state that it is displaced from the top face of the base 2. Concretely, the frame part 11 has multiple leg parts 11a standing on the top face of the base 2, and a holding part 11b disposed on the tip ends of the multiple leg parts 11a. The holding part 11b is formed with an accommodation hole 11h into which the holding plate 12 is to be set (see FIG. 2). The accommodation hole 11h is formed with a supporting edge 11f on a flange, at the open end edge on the side of the base 2.

Since the frame part 11 has such a structure, by setting the holding plate 12 in the accommodation hole 11h of the holding part 11b, it is possible to keep the holding plate 12 at a position distanced from the top face of the base 2 by approximately the length of the multiple leg parts 11a.

The frame part 11 is only required to be able to hold the holding plate 12 in the state that it is distanced from the top face of the base 2 for allowing formation of the measurement space 1h, and its structure is not limited to the aforementioned structure. For example, the holding part 11b may be supported by a single leg part 11a, or the holding part 11b may be supported by multiple walls in place of the leg parts 11a. The ability to hold the holding plate 12 is desired to prevent occurrence of motion, vibration or the like that will cause a measurement error, particularly during operation of the moving mechanism 20. When the holding part 11b is supported by the multiple walls, leakage of the radiation can be prevented because the interior of the measurement space 1h can be hermetically sealed to some extent, however, the sensor can drift due to the temperature elevation in the measurement space 1h. Therefore, when the holding part 11b is supported by multiple walls, it is desired to provide a fan or the like for cooling the measurement space 1h.

The method for holding the holding plate 12 positioned in the accommodation hole 11h is not particularly limited. By providing the supporting edge 11f as described above, it is possible to position the holding plate 12 in the accommodation hole 11h by placing the holding plate 12 on the supporting edge 11f.

Further, a groove or the like may be formed in the circumferential edge part of the holding plate 12, and a projection that can be accommodated in the groove may be provided in the inner face of the accommodation hole 11h. This structure further gives the merit of achieving positioning while supporting the holding plate 12 by the projection.

(Holding Plate 12)

Figure 8:
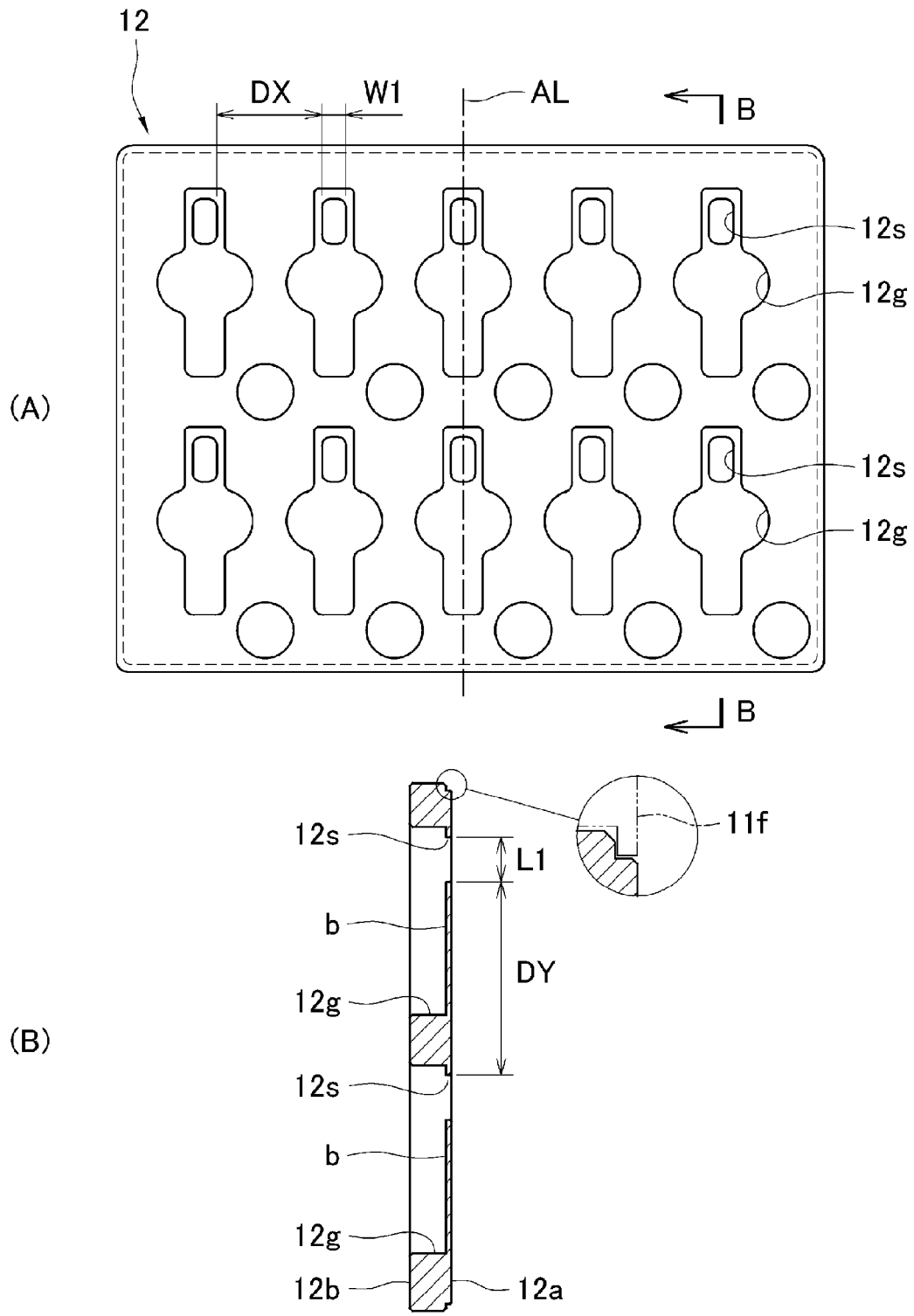

As illustrated in FIG. 8, the holding plate 12 is a member formed, for example, of stainless as a raw material, and is formed of a plate-like member. The holding plate 12 has a substantially similar shape to the accommodation hole 11h of the holding part 11b of the frame part 11 as described above, and is formed to be slightly smaller than the accommodation hole 11h. Concretely, it is formed into such a size that the holding plate 12 will little rattle in the accommodation hole 11h in the state that the holding plate 12 is positioned in the accommodation hole 11h. For example, it is so formed that when the holding plate 12 is positioned in the accommodation hole 11h, a gap Da formed between the holding plate 12 and the inner face of the accommodation hole 11h is about 0.06 to 0.12 mm (see FIG. 1). By forming the holding plate 12 to have such a shape and size, it is possible to prevent occurrence of motion, vibration or the like that will cause a measurement error in the holding plate 12 during operation of the moving mechanism 20 which is described later. Also, even if the position where the holding plate 12 is positioned in the accommodation hole 11h deviates slightly, occurrence of a measurement error caused by the positional deviation can be prevented.

When the aforementioned structure in which the holding plate 12 is supported by the supporting edge 11f is employed, a step may be provided in a later-described opposed face 12a of the holding plate 12 as illustrated in FIG. 8(B). That is, the structure that the step is caught by the supporting edge 11f when the holding plate 12 is positioned in the accommodation hole 11h may be employed (see the part enclosed by the circle in FIG. 8(B)). In this case, the holding plate 12 can be made into a more stable state in the accommodation hole 11h, and the opposed face 12a of the holding plate 12 can be made substantially flush with the surface of the holding part 11b, so that it becomes easier to move the radiation intensity measuring means 30 toward the opposed face 12a of the holding plate 12.

Also, as illustrated in FIG. 8, the holding plate 12 is formed with multiple accommodation grooves 12g. The multiple accommodation grooves 12g are provided in multiple columns and multiple rows. The multiple accommodation grooves 12g are formed to be substantially parallel with each other. Concretely, they are provided so that the axial directions AL of the accommodation grooves 12g are parallel with each other. The axial directions AL of the accommodation grooves 12g are parallel with the y direction in FIG. 1 when the holding plate 12 is positioned in the accommodation hole 11h (see FIG. 1).

The accommodation groove 12g is formed to be recessed from one face of the holding plate 12 (left face in FIG. 8(B), hereinafter referred to as a supply face 12b) toward the other face (right face in FIG. 8, hereinafter referred to as an opposed face 12a). The accommodation groove 12g is so provided that the axial direction of the cartridge C is substantially parallel with the axial direction AL of the accommodation groove 12g when the container PK is put into the accommodation groove 12g in such a manner that the top face of the container PK (top face in FIG. 10) faces with an inner bottom face b of the accommodation groove 12g. In other words, it is so provided that the arrangement direction of the radiation sources S packed in the cartridge C is substantially parallel with the axial direction AL of the accommodation groove 12g, and the axial direction of the radiation source S is substantially parallel with the opposed face 12a.

For example, the supply face 12b and the opposed face 12a of the holding plate 12 are formed parallel with each other. And the depth of the accommodation groove 12g is preliminarily adjusted so that the top face of the flange part f is almost in surface contact with the supply face 12b when the container PK is put into the accommodation groove 12g. As a result, it is possible to bring the posture of the radiation source S into the state as described above by putting the container PK into the accommodation groove 12g.

In addition, the accommodation groove 12g is formed into such a shape that the container PK put into the accommodation groove 12g as described above will not move.

For example, when the inner lateral face of the accommodation groove 12g is formed to have substantially the same shape as the outer lateral face of the accommodation case PC of the container PK, the container PK can be accommodated in such a manner that it will not move in the accommodation groove 12g while the posture of the radiation source S is brought into the state as described above.

The shape of the accommodation groove 12g is not particularly limited as far as it can accommodate the container PK immovably in the accommodation groove 12g. For example, the container PK can be held in the accommodation groove 12g immovably also by providing a part capable of sandwiching and holding the recess part d of the accommodation case PC of the container PK.

In this accommodation groove 12g, at the position corresponding the position where the seed cartridge SC is located when the container PK is positioned in the accommodation groove 12g (the seed cartridge SC corresponding position), a radiation emitting part 12s is provided. Concretely, the radiation emitting part 12s is formed so that the radiation emitting part 12s and the seed cartridge SC almost overlap with each other in a plan view when the container PK is positioned in the accommodation groove 12g.

Figure 7:
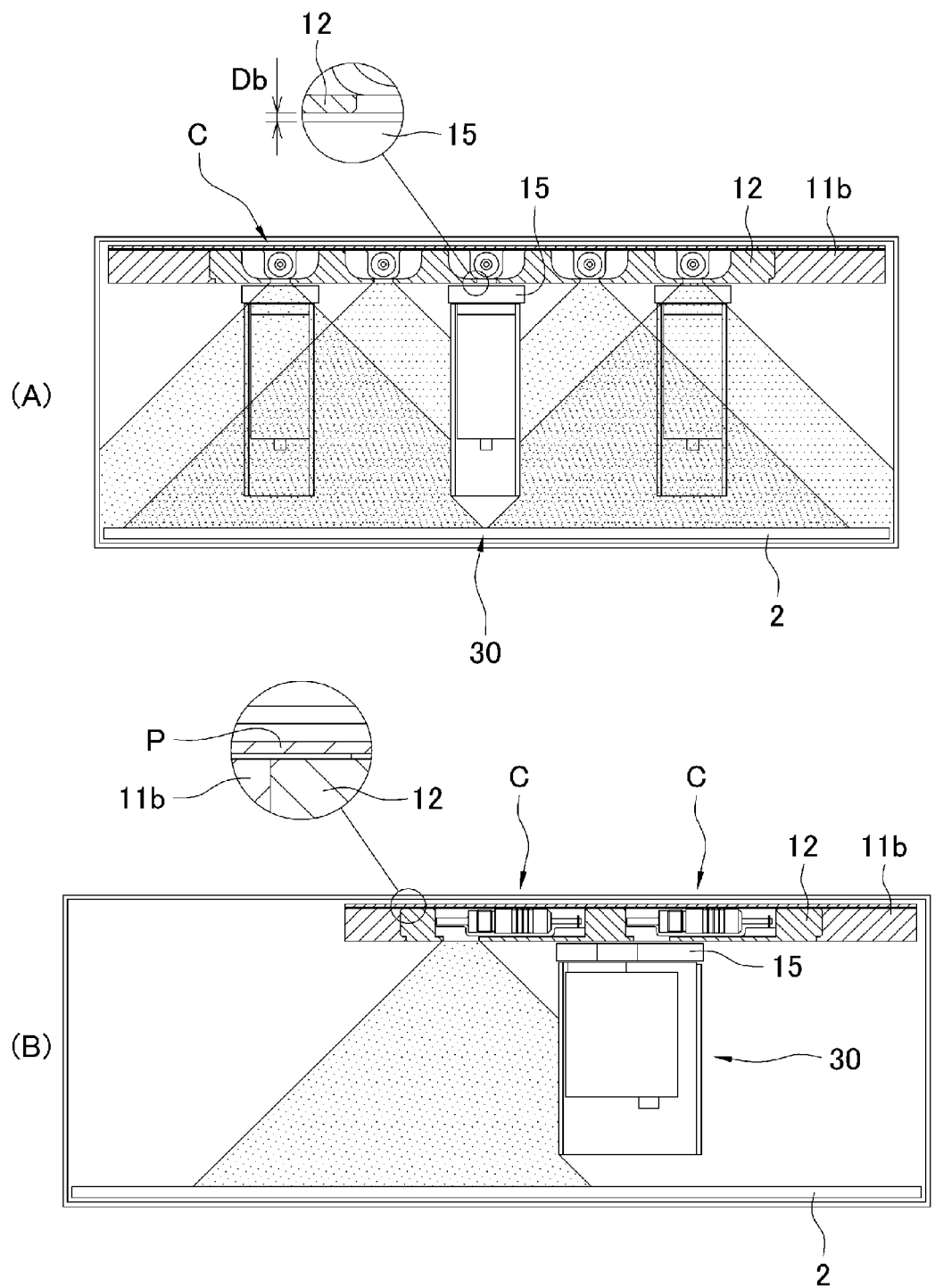
FIG. 7 are schematic explanatory views illustrating areas of radiation emitted from respective radiation emitting parts 12f.

The radiation emitting part 12s is provided for emitting the radiation emitted from the radiation source S, to the measurement space 1h from the opposed face 12a (see FIG. 7). Concretely, the accommodation groove 12g is formed so that its inner bottom face has such a thickness (distance from the inner bottom face b to the opposed face 12a) that the radiation emitted from the radiation source S cannot transmit therethrough. On the other hand, at the position corresponding to the seed cartridge SC of the accommodation groove 12g, a through hole that penetrates the inner bottom face b of the accommodation groove 12g and the opposed face 12a is formed as the radiation emitting part 12s.

As a result, when the container PK is positioned inside the accommodation groove 12g, the radiation emitted from the radiation source S passes through only the radiation emitting part 12s and is irradiated inside the measurement space 1h (see FIG. 7). In addition, since the radiation emitting part 12s is provided to almost overlap with the seed cartridge SC in a plan view, the radiation emitted from the radiation source S directly passes through the radiation emitting part 12s. Accordingly, attenuation of radiation in passing through the radiation emitting part 12s can be suppressed, and thus measurement of the radiation intensity by the later-described radiation intensity measuring means 30 can be accurately executed.

For example, in the stainless-steel holding plate 12, the thickness of the inner bottom face b of the inner accommodation groove 12g is about 1.9 to 2.1 mm, and the distance from the opposed face 12a to the seed cartridge SC in the state that the container PK is positioned in the accommodation groove 12g is about 7.4 to 7.6 mm. And the length L1 in the axial direction of the radiation emitting part 12s (in other words, the axial direction of the accommodation groove 12g) is about 8.5 to 8.7 mm, and the length W1 in the width direction is about 15.9 to 16.1 mm. Then, the radiation emitted from the radiation source S is partly shielded by the holding plate 12, however, most of the radiation can be irradiated in the measurement space 1h. Also, it is possible to reduce the proportion of the radiation emitted from the radiation emitting part 12s in the radiation reflected in the accommodation groove 12g.

The radiation emitting part 12s is not necessarily a through hole as described above. The radiation intensity measuring part may have any structure as far as it can transmit the radiation emitted from the radiation source S, and can grasp the radiation intensity emitted from the radiation source S by measuring the intensity of the transmitted radiation by means of the radiation intensity measuring means 30. For example, only the part of the radiation emitting part may be made of a material easily transmitting radiation, or only the part of the radiation emitting part may have a very small thickness compared with the remaining part of the accommodation groove 12g. However, by embodying the radiation emitting part by the through hole as described above, the structure of the holding plate 20 can be simplified, and the merit of reducing attenuation of radiation between the multiple radiation sources S and the sensor is obtained.

Also, the holding plate 12 may have a cover plate which is attached to the supply face 12b thereof. By using a cover plate having a structure capable of suppressing motion of the container PK in the accommodation groove 12g when attached to the supply face 12b, it is possible to securely prevent the container PK from moving in the accommodation groove 12g during measurement.

For example, the accommodation groove 12g is formed so that the flange part f of the container PK is positioned in surface contact with the supply face 12b. In this case, as illustrated in FIG. 7, by attaching the plate-like cover plate PT to the supply face 12b of the holding plate 12, it is possible to sandwich and hold the flange part f between the cover plate PT and the supply face 12b (see FIG. 7). And thus, it is possible to securely prevent the container PK from moving inside the accommodation groove 12g.

In particular, when the cover plate is made of a material that does not transmit radiation or the cover plate has such a thickness that does not transmit radiation, it is possible to prevent the radiation from being emitted outside from the side of the supply face 12b. In this case, when the radiation intensity measuring apparatus 1 according to the present embodiment is positioned inside a case or the like, it is easier to prevent the radiation leakage to the outside.

(Moving Means 20)

Figure 3:
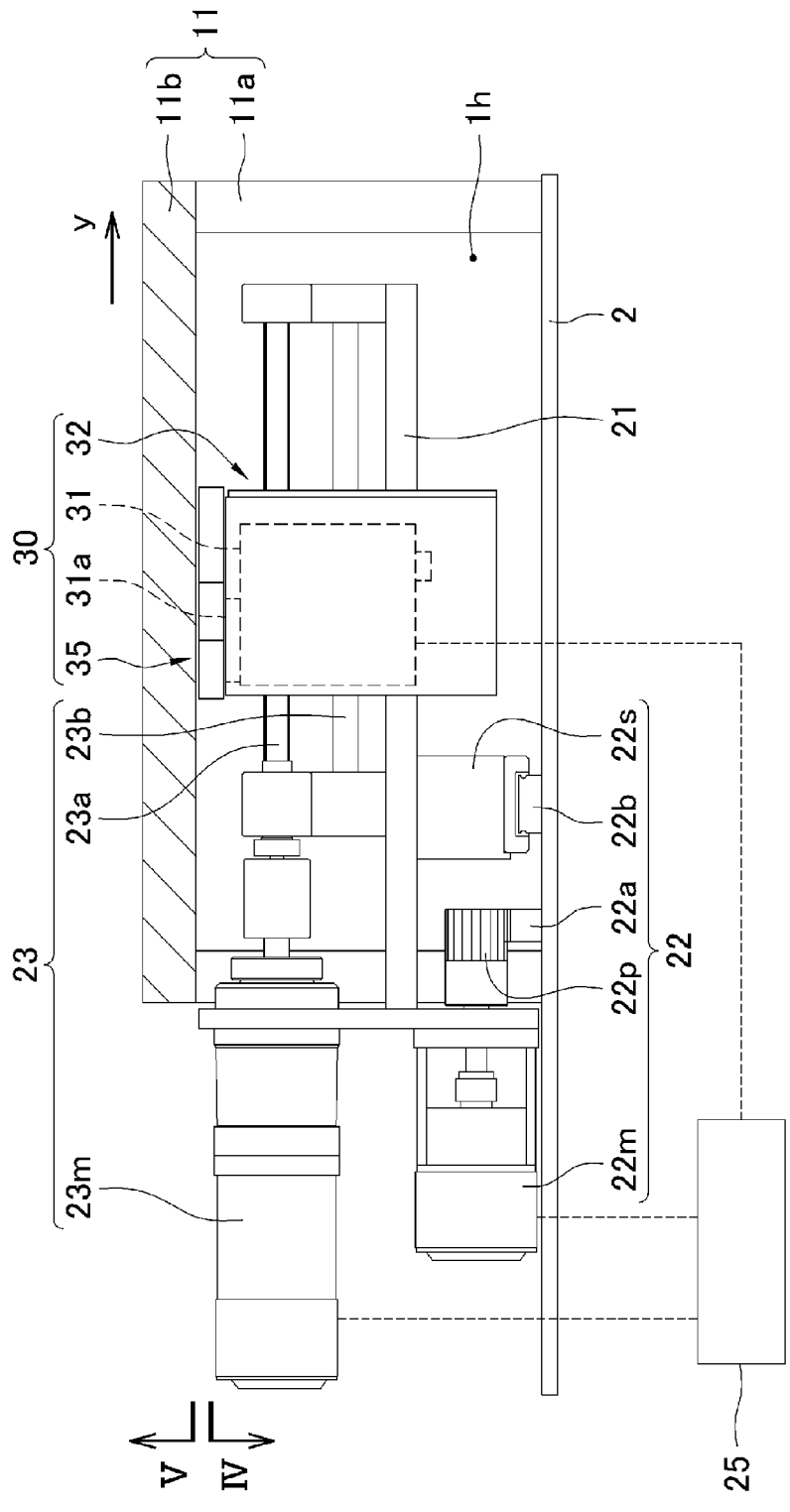
FIG. 3 is a sectional arrow view along the line in FIG. 1.

As illustrated in FIG. 3, in the measurement space 1h between the base 2 and the holding plate 12, the moving mechanism 20 is provided. The moving mechanism 20 includes a moving frame 21, an x-direction moving mechanism 22 for moving the radiation intensity measuring means 30 in the x direction, a y-direction moving mechanism 23 for moving the radiation intensity measuring means 30 in the y direction, and a controller 25 for controlling operations of the x-direction moving mechanism 22 and the y-direction moving mechanism 23.

Figure 1:
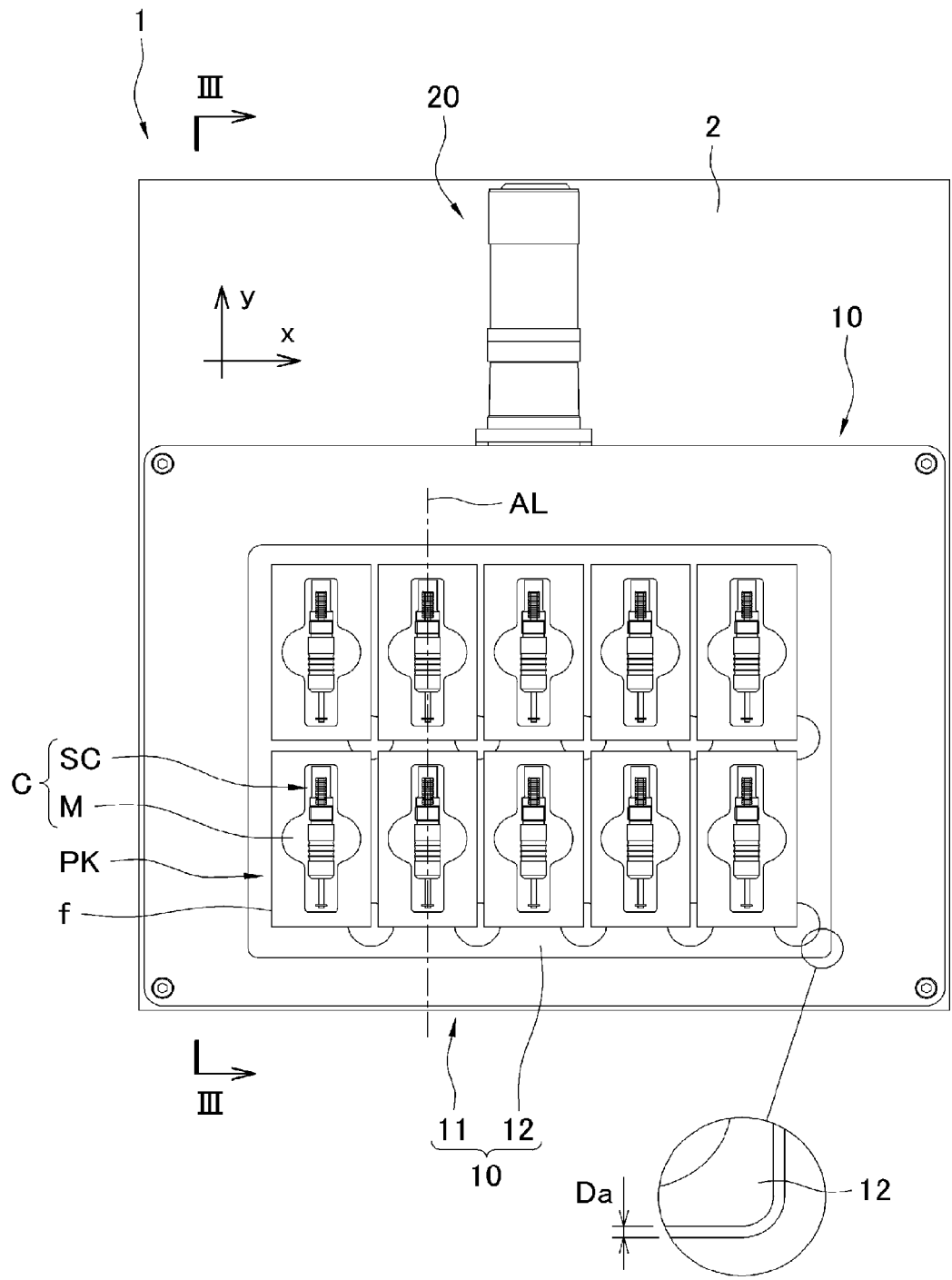
FIG. 1 is a schematic plan view of a radiation intensity measuring apparatus 1 for small sealed radiation sources for cancer therapy according to the present embodiment.
Figure 2:
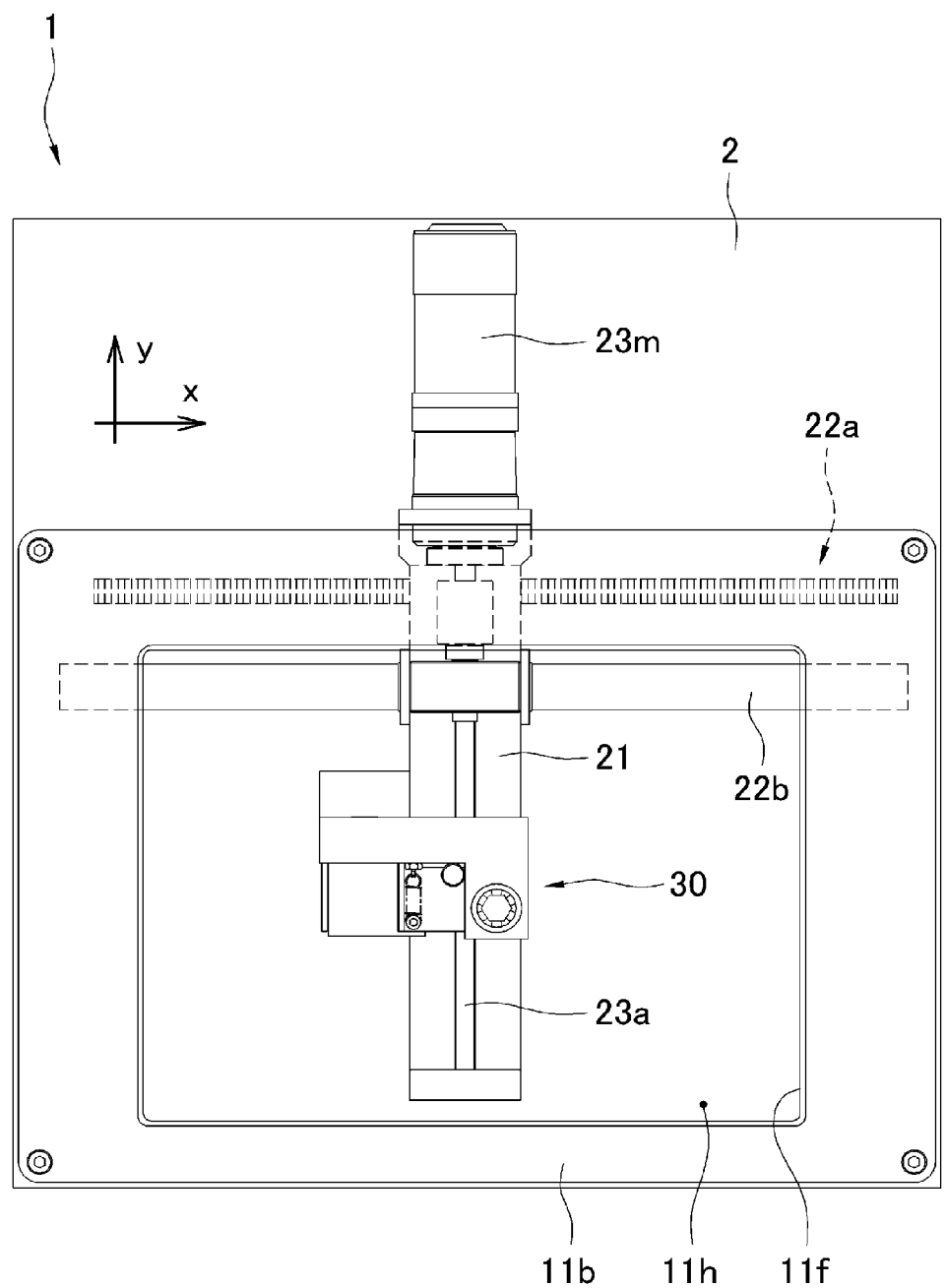
FIG. 2 is a schematic plan view of a radiation intensity measuring apparatus 1 for small sealed radiation sources for cancer therapy according to one embodiment, in the state that a holding plate 12 is detached.

The y direction used herein is the y direction shown in FIG. 1, and is parallel with the axial direction of the accommodation groove 12h of the holding plate 12 when the holding plate 12 is positioned in the accommodation hole 11h of the holding part 11b of the frame part 11. In other words, the y direction means the direction parallel with the arrangement direction of the radiation sources S that are hermetically sealed in the container PK and accommodated in the cartridge C accommodated in the accommodation groove 12h of the holding plate 12. The x direction means the direction that is parallel with the opposed face 12a of the holding plate 12 when the holding plate 12 is positioned in the accommodation hole 11h of the holding part 11b of the frame part 11, and is orthogonal to the y direction.

(X-Direction Moving Mechanism 22)

As illustrated in FIG. 3, on the top face of the base 2, a rack 22a and a rail 22b of the x-direction moving mechanism 22 are provided along the x direction. The rail 22b is provided with a slider 22s that is movable along the axial direction of the rail 22b. The slider 22s is fixed to the moving frame 21 as described above. To the moving frame 21, an x-direction driving motor 22m such as a stepping motor is attached. The x-direction driving motor 22m is provided so that its main shaft is parallel with the y direction. To the main shaft of the x-direction driving motor 22m, a pinion 22p is attached, and the pinion 22p meshes with the rack 22a.

Therefore, by operating the x-direction driving motor 22m, it is possible to move the moving frame 21 along the axial direction of the rack 22a (x direction) together with the x-direction driving motor 22m in association with the rotation of the pinion 22p. In addition, since the moving frame 21 is supported by the rail 22b via the slider 22s, the moving frame 21 can be moved stably and smoothly along the x direction.

(Y-Direction Moving Mechanism 23)

Figure 4:
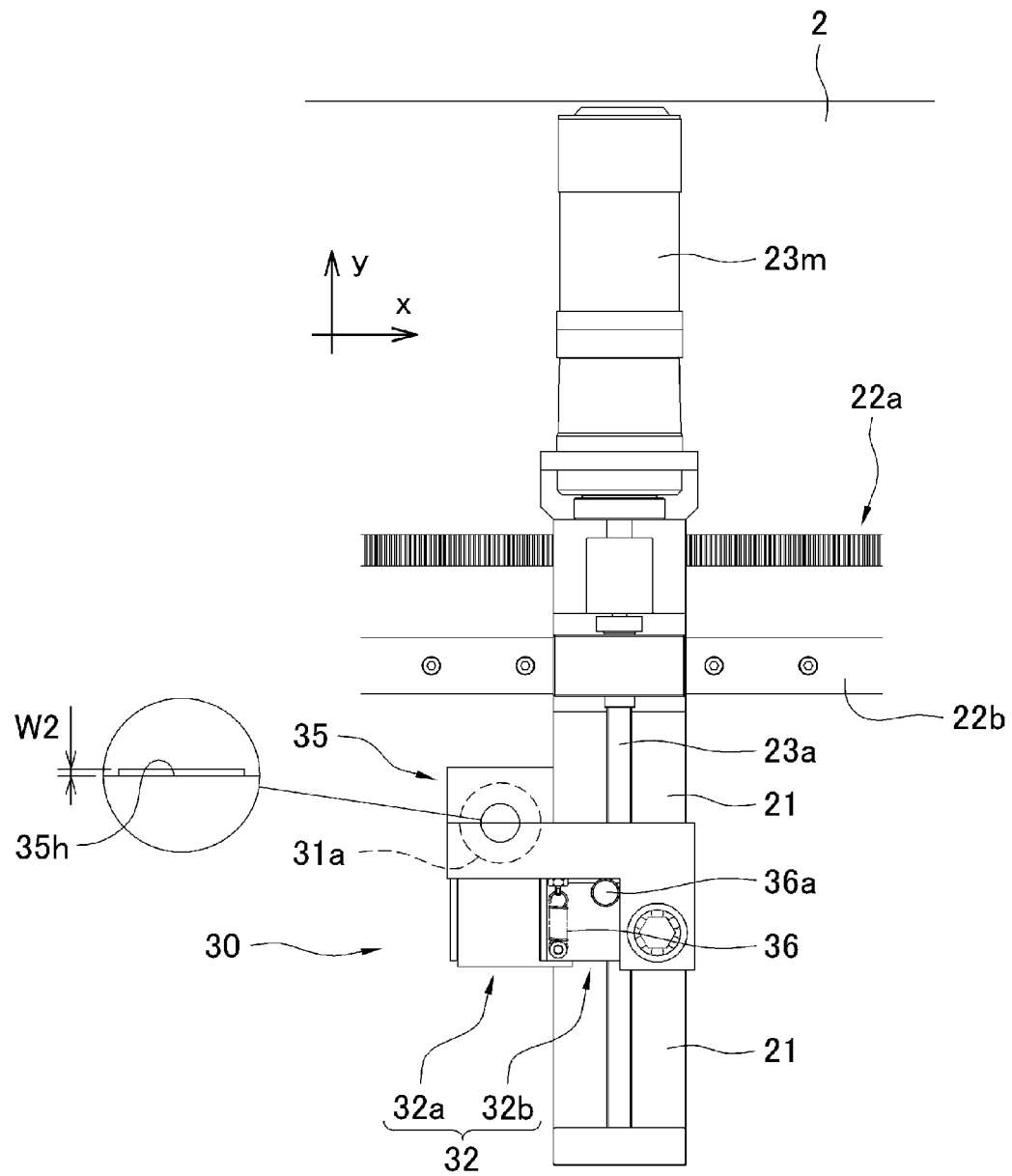
FIG. 4 is an arrow view of an essential part along the line IV in FIG. 3.

As illustrated in FIG. 3 and FIG. 4, to the moving frame 21, a y-direction driving motor 23m such as a stepping motor is attached. The y-direction driving motor 23m is provided so that its main shaft is parallel with the y direction. To the main shaft of the y-direction driving motor 23m, a screw shaft 23a is connected. The screw shaft 23a is attached to the moving frame 21 so that it is in parallel with the y direction. To the screw shaft 23a, a male screw formed in the later-described radiation intensity measuring means 30 is screwed together.

Therefore, by operating the y-direction driving motor 23m to rotate the screw shaft 23a, it is possible to move the radiation intensity measuring means 30 along the axial direction of the screw shaft 23a (y direction) in association with the rotation of the screw shaft 23a.

(Controller 25)

As illustrated in FIG. 3, the x-direction driving motor 22m of the x-direction moving mechanism 22 and the y-direction driving motor 23m of the y-direction moving mechanism 23 are electrically connected with the controller 25. The controller 25 controls the operation amounts (namely, rotation amount, rotation direction, operation timing) of the x-direction driving motor 22m and the y-direction driving motor 23m.

The controller 25 stores the information about the position where the radiation emitting part 12s of each accommodation groove 12g is located when the holding plate 12 is positioned in the accommodation hole 11h of the holding part 11b of the frame part 11, and about the axial direction of each accommodation groove 12g. Based on the information, the controller 25 controls the operations of the x-direction driving motor 22m and the y-direction driving motor 23m so that the radiation intensity of the radiation source S of the cartridge C accommodated in each accommodation groove 12g is sequentially measured by the radiation intensity measuring means 30.

By operating the x-direction driving motor 22m and the y-direction driving motor 23m of the moving mechanism 20 by the controller 25 in the manner as described above, it is possible to move the radiation intensity measuring means 30 in the y direction while moving the moving frame 21 in the x direction. That is, by appropriately operating the x-direction driving motor 22m and the y-direction driving motor 23m by the controller 25, it is possible to position the radiation intensity measuring means 30 at a predetermined position on the xy plane (that is, the plane parallel with the opposed face 12a of the holding plate 12) in the measurement space 1h, and it is possible to move the radiation intensity measuring means 30 in a desired direction along the xy plane. By operating only one of the x-direction moving mechanism 22 and the y-direction moving mechanism 23 while stopping operation of the other of the same, it is possible to move the radiation intensity measuring means 30 along the x direction or the y direction.

Therefore, by moving the radiation intensity measuring means 30 by the moving mechanism 20, it is possible to sequentially measure the radiation intensity of the radiation sources S in the cartridge C accommodated in each accommodation groove 12g by the radiation intensity measuring means 30.

The moving frame 21 may be provided with a guide axis 23b provided parallel with the screw shaft 23a, and the radiation intensity measuring means 30 may be attached to the guide axis 23b so as to be movable along the axial direction of the guide axis 23b. As a result, it is possible to move the radiation intensity measuring means 30 along the y direction while it is supported at least at two points, and thus it is possible to move the radiation intensity measuring means 30 in a stable posture.

The configuration of the moving mechanism 20 is not limited to the aforementioned configuration, and any mechanism capable of moving the radiation intensity measuring means 30 parallel with the plane that is parallel with the opposed face 12a of the holding plate 12 can be employed. For example, a screw-nut mechanism can be employed as the x-direction moving mechanism, and a rack-pinion mechanism can be employed as the y-direction moving mechanism. Further, the moving frame 21 can be moved by a cylinder mechanism.

(Radiation Intensity Measuring Means 30)

As illustrated in FIG. 3 and FIG. 4, the radiation intensity measuring means 30 has a sensor 31 for measuring radiation intensity, a sensor holding part 32 for holding the sensor 31, and a shielding member 35 provided for restricting the radiation irradiated to the sensor 31.

First, the sensor 31 has a detecting part 31a for measuring radiation intensity on its one face. The sensor 31 has a function of converting the intensity of the radiation irradiated to the detecting part 31a into an electric signal and outputting the electric signal.

The sensor holding part 32 is a member for holding the sensor 31. The sensor holding part 32 has a supporting part 32a for supporting the sensor 31, and a connecting part 32b for connecting the supporting part 32a to the moving mechanism 20.

First, to the supporting part 32a, the sensor 31 is attached. Concretely, the sensor 31 is attached to the supporting part 32a in such a manner that the detecting part 31a of the sensor 31 faces with the opposed face 12a of the holding plate 12. In addition, the supporting part 32a has a lateral wall provided to cover the lateral face of the sensor 31, and thus prevents the radiation from being irradiated to the detecting part 32a of the sensor 31 from the lateral side.

The supporting part 32a is connected to the moving mechanism 20 by the connecting part 32b. Concretely, the connecting part 32b is formed with a female screw hole, and a guide hole provided parallel with the female screw hole. And the screw shaft 23a is screwed into the female screw hole, and the guide axis 23b is penetrated in the guide hole.

Therefore, as the screw shaft 23a rotates, the connecting part 32b moves along the screw shaft 23a, so that it is possible to move the sensor 31 fixed to the supporting part 32a that is connected to the connecting part 32b along the axial direction (y direction) of the screw shaft 23a.

As illustrated in FIG. 3 and FIG. 4, the shielding member 35 is provided to cover the detecting part 31a of the sensor 31 held by the sensor holding part 32. In other words, the shielding member 35 is provided so that it is positioned between the detecting part 31a of the sensor 31 held by the sensor holding part 32, and the opposed face 12a of the holding plate 12. The shielding member 35 restricts the radiation irradiated to the detecting part 31a of the sensor 31 when the radiation is emitted from the radiation emitting part 12s of the holding plate 12.

Concretely, the shielding member 35 is a member formed of a material that radiation fails to transmit or difficult to transmit therethrough (for example, brass, copper, tungsten and so on) or a stainless plate, formed into a material having a thickness through which the radiation cannot transmit (for example, about 7 to 9 mm). The shielding member 35 is formed with a slit 35h. The slit 35h is formed to pass through the face opposed to the opposed face 12a of the holding plate 12 (shielding face) and the face opposed to the detecting part 31a of the sensor 31 in the shielding member 35. That is, by providing the shielding member 35, only the radiation passing through the slit 35h of the radiation emitted from the radiation emitting part 12s of the holding plate 12 is irradiated to the detecting part 31a of the sensor 31 when the radiation intensity measuring means 30 is positioned below the radiation emitting part 12s of the holding plate 12.

The slit 35h is formed so that its axial direction is parallel with the x direction in the state that the radiation intensity measuring means 30 is attached to the moving means 20. That is, the slit 35h is formed in the direction orthogonal to the arrangement direction of the radiation sources S, or in other words, in the direction parallel with the axial directions of the radiation sources S. In addition, the slit 35h is formed so that its width W2 is smaller than the wire diameter of the radiation source S.

With the above configuration, the radiation intensity measuring means 30 is moved below the radiation emitting part 12s of the accommodation groove 12g in which the cartridge C to be measured is accommodated, and the radiation intensity measuring means 30 is moved along the axial direction of the accommodation groove 12g (that is, the arrangement direction of the radiation sources S) by means of the moving mechanism 20. As a result, it is possible to measure the intensity of the radiation emitted from the multiple radiation sources S packed in the cartridge C to be measured.

In addition, the width W2 (see FIG. 4) of the slit 35h is smaller than the wire diameter of the radiation source S, and the axial direction of the slit 35h is parallel with the axial direction of the radiation source S. Therefore, when the radiation intensity measuring means 30 is moved along the axial direction of the accommodation groove 12g (that is, the arrangement direction of the radiation sources S), the radioactivity of each radiation source S can be calculated based on the variation in radiation intensity of the radiation source S detected by the detecting part 31a of the sensor 31. For example, the slit 35h may have the width W2 ranging from 0.05 to 0.15 mm, and the axial length ranging from 9 to 11 mm.

In measuring the radiation intensity of the radiation source S held by the aforementioned cartridge C3, there is the case where one accommodation groove 12g is provided with multiple radiation emitting parts 12s. In this case, the cartridge C3 is positioned so that each one of the radiation sources S is allocated to each radiation emitting part 12s. Then, by means of the moving mechanism 20, the radiation intensity measuring means 30 is sequentially moved below each radiation emitting part 12s in the accommodation groove 12g where the cartridge C to be measured is accommodated, and the radiation intensity measuring means 30 is moved along the direction intersecting with the axial direction of each radiation source S (preferably, the direction orthogonal to the axial direction of the radiation source S). Thus, the intensity of the radiation emitted from each radiation source S packed in the cartridge C3 to be measured can be individually measured.

In measuring the radiation intensity of the radiation source S held by the aforementioned shaft-shaped cartridge C3, as described above, the slit-like radiation emitting part 12s may be provided in place of providing multiple radiation emitting parts 12s in one accommodation groove 12g. Also in this case, the radiation intensity measuring means 30 is sequentially moved below each radiation source S in the cartridge C3 to be measured by means of the moving mechanism 20. For each radiation source S, by moving the radiation intensity measuring means 30 along the direction intersecting with the axial direction thereof (preferably, the direction orthogonal to the axial direction of the radiation source S), it is possible to individually measure the intensity of the radiation emitted from each radiation source S packed in the cartridge C to be measured.

Further, the shielding member 35 of the radiation intensity measuring means 30 is preferably provided so that the shielding face thereof on the side of the holding plate 12 is parallel with the opposed face 12a of the holding plate 12. Since the radiation intensity measuring means 30 moves parallel with the opposed face 12a by means of the moving mechanism 20, interference between the holding plate 12 and the shielding member 35 can be prevented even when the gap between the holding plate 12 and the shielding member 35 is narrowed in the aforementioned configuration of the shielding member 35. In other words, it is possible to reduce the distance between the opposed face 12a of the holding plate 12 and the shielding member 35. As a result, it is possible to prevent the radiation having passed through the neighboring radiation emitting part 12s from being irradiated to the sensor face 31a of the sensor 31 through the slit 35h during measurement of the radiation passing through one radiation emitting part 12s. For example, the radiation emitting part 12s has the size as described in the paragraph 0074, and the slit 35h has the size as described in the paragraph 0096. In this case, as shown in FIG. 7, radiation is emitted from each radiation emitting part 12s. By setting the gap Db between the holding plate 12 and the shielding member 35 at 0.5 to 1.5 mm, it is possible to prevent the radiation having passed through the neighboring radiation emitting part 12s from being irradiated to the sensor face 31a of the sensor 31 through the slit 35h even if the distance DX in the x direction between the neighboring radiation emitting parts 12s is set at 45 to 47 mm, and the distance DY in the y direction is set at 84 to 86 mm (see FIG. 8).

The opposed face 12a of the holding plate 12 as described above corresponds to the reference face in claim 9.

(Radiation Intensity Measuring Operation)

Next, measurement of the radiation intensity by the radiation intensity measuring apparatus 1 according to the present embodiment will be specifically described.

First, in each multiple accommodation groove 12g in the holding plate 12, the container PK is accommodated, and the holding plate 12 is positioned in the accommodation hole 11h of the holding part 11b. Then in each cartridge C accommodated in the multiple accommodation grooves 12g, the arrangement direction of the packed multiple radiation sources S substantially coincides with the axial direction AL of each accommodation groove 12g. Therefore, in the state that the holding plate 12 is positioned in the accommodation hole 11h of the holding part 11b, the arrangement direction of the multiple radiation sources S packed in each cartridge C is parallel with the y direction, and the axial directions of the multiple radiation sources S are parallel with the x direction.

On the other hand, the slit 35h of the shielding member 35 of the radiation intensity measuring means 30 is formed so that its axial direction is parallel with the x direction. Therefore, the radiation intensity measuring means 30 is moved by the x-direction moving mechanism 22 to the position where the plane dividing the slit 35h into two halves in its axial direction contains the axial direction AL of one accommodation groove 12g. And thus, preparation for measuring the radiation intensity of the multiple radiation sources S packed in the cartridge C accommodated in one accommodation groove 12g completes.

Hereinafter, the state that the radiation intensity measuring means 30 is positioned as described above for each accommodation groove 12g is referred to as a measurement standby state.

Then as the radiation intensity measuring means 30 is positioned in the measurement standby state, the radiation intensity measuring means 30 is moved in the y direction by means of the y-direction moving mechanism 23. Then, the slit 35h passes below the radiation emitting part 12s of one accommodation groove 12g while keeping its axial direction parallel with the axial direction of the multiple radiation sources S. And thus, the intensity of the radiation emitted from each of the multiple radiation sources S packed in the cartridge C accommodated in one accommodation groove 12g is measured by the detecting part 31a of the sensor 31. At this time, since the width of the slit 35h is formed to be smaller than the wire diameter of the radiation source S, the radiation intensity detected by the detecting part 31a of the sensor 31 varies with the movement of the slit 35h.

Concretely, since the width of the slit 35h is smaller than the wire diameter of the radiation source S, only part of the radiation emitted from the radiation source S passes through the slit 35h, and only the radiation having passed through the slit 35h is detected by the detecting part 31a of the sensor 31. Since the radiation emitted from the radiation source S is emitted radially from the center axis of the radiation source S (see FIG. 7), the radiation intensity detected by the detecting part 31a of the sensor 31 peaks when the center axis of the slit 35h and the center axis of the radiation source S coincide with each other, and decreases as the deviation therebetween increases. Therefore, the radiation intensity detected by the detecting part 31a of the sensor 31 varies with the movement of the slit 35h as far as the axial direction of the slit 35h is kept parallel with the axial direction of the radiation source S during its movement. That is, the radiation intensity varies in such manner that it peaks when the center axis of the slit 35h coincides with the center axis of each radiation source S, and reaches a trough when the center axis of the slit 35h is positioned between the center axes of the neighboring radiation sources S.

As a result, it is possible to calculate the radioactivity of each radiation source S based on the variation in measured radiation intensity, concretely, the number of peaks of the radiation intensity, the peak value, and the peak timing.

After completion of measurement of all the radiation sources S packed in the cartridge C accommodated in one accommodation groove 12g, the radiation intensity measuring means 30 is moved by the moving mechanism 20 so that the accommodation groove 12g in which the cartridge C to be measured next is accommodated is brought into the measurement standby state. Then, as the radiation intensity measuring means 30 is positioned in the measurement standby state, the radiation intensity measuring means 30 is moved in the y direction by the moving mechanism 20. Then, the intensity of the radiation emitted from the multiple radiation sources S packed in the cartridge C accommodated in the accommodation groove 12g is measured by the detecting part 31a of the sensor 31.

After completion of measurement of the multiple radiation sources S packed in the cartridge C accommodated in this accommodation groove 12g, the radiation intensity measuring means 30 is moved so that the accommodation groove 12g in which the cartridge C to be measured next is accommodated is brought into the measurement standby state, and then the radiation intensity is measured.

The above-described operation is repeated until measurement of the radiation sources S packed in all the cartridges C completes. After completion of measurement of the radiation sources S packed in all the cartridges C, the holding plate 12 is detached from the frame part 11, and the next holding plate 12 is positioned. At this time, by preliminarily setting the container PK in the next accommodation groove 12g of the holding plate 12, it is possible to replace the cartridges C to be measured only by positioning the next holding plate 12.

In addition, since plural cartridges C can be replaced at once, it is possible to replace the cartridge C to be measured in a very short time, and to suppress the radiation exposure to the operator.

According to the radiation intensity measuring apparatus 1 of the present embodiment having the aforementioned configuration, by accommodating the cartridge C in which the multiple radiation sources S are packed in the accommodation groove 12g, and moving the radiation intensity measuring means 30 by the moving mechanism 20, it is possible to measure the radiation intensity of each radiation source S at one measurement while keeping the multiple radiation sources S (that is, all the radiation sources S packed in the cartridge C) packed in the cartridge C. Therefore, it is possible to measure the radioactivity of the multiple radiation sources S packed in the cartridge C in a short time.

Further, since the variation in the radiation intensity is measured by moving the slit 35h (that is, radiation intensity measuring means 30), it is possible to grasp a peak value or the presence or absence of a peak value in the variation curve of the radiation intensity even when there is some variation in the packing interval of the radiation sources S.

Therefore, even if the position of the radiation source S held in the cartridge C is somewhat misaligned, it is possible to measure the radiation intensity of each radiation source S accurately.

The speed at which the radiation intensity measuring means 30 moves in the arrangement direction of the radiation sources S is not particularly limited, and may be any speed at which variation in the radiation intensity required for calculation of the radioactivity of each radiation source S can be measured.

Further, since the multiple cartridges C are held in the holding plate 12, it is possible to sequentially move the radiation intensity measuring means 30 so that the holding groove 12g accommodating each cartridge C is brought into the measurement standby state, and it is possible to sequentially measure the radiation intensity of the multiple radiation sources S in each cartridge C. By moving the radiation intensity measuring means 30 by the moving mechanism 20, it is possible to successively measure the radiation intensity of the multiple radiation sources S in the multiple cartridges C.

When only part of the radiation sources S among the multiple radiation sources S packed in the cartridge C are intended to be measured, it is not necessary to make the slit 35h pass through the position of every radiation source S, but it is only required to move the radiation intensity measuring means 30 so that the slit 35h passes through the position of the radiation source S that is intended to be measured.

Similarly, in the case of measuring only the multiple radiation sources S packed in part of cartridges C held in the holding plate 12, only the target cartridge C may be measured.

The aforementioned state from positioning the radiation intensity measuring means 30 in one accommodation groove 12g to establish the measurement standby state, to completion of measurement of the radiation intensity for the radiation sources S packed in the cartridge C accommodated in the one accommodation groove 12g corresponds to a measurement state described in claims.

In the aforementioned embodiment, the shielding face of the shielding member 35 is kept parallel with the opposed face 12a of the holding plate 12 and also the axial direction of the slit 35h is kept parallel with the x direction in the state other than the measurement state. However, the posture of the shielding face of the shielding member 35 and the positioning in the axial direction of the slit 35h in the state other than the measurement state are not particularly limited.

(Regarding Measurement Accuracy)

In the measurement standby state, the radiation intensity measuring means 30 is moved by the x-direction moving mechanism 22 to the position where the plane dividing the slit 35h into two halves in its axial direction contains the axial direction AL of one accommodation groove 12g, and then the radiation intensity measuring means 30 is moved in the y direction. By moving the radiation intensity measuring means 30 in this manner, it is possible to accurately measure the intensity of the radiation emitted from the radiation source S. However, in the measurement standby state, even when the plane dividing the slit 35h into two halves in its axial direction is slightly (for example, about 1 mm) deviated from the axial direction AL of one accommodation groove 12g, the measurement accuracy of the intensity of the radiation emitted from the radiation source S does not significantly deteriorate as far as the axial length of the slit 35h is 9 to 11 mm. Also, even when the moving direction is slightly (for example, about 5 degrees) tilted from the y direction in moving the radiation intensity measuring means 30 from the measurement standby state, the measurement accuracy of the intensity of the radiation emitted from the radiation source S does not significantly deteriorate.

On the other hand, when deviation in positioning the holding plate 12 in the accommodation hole 11h of the holding part 11b, deviation in putting the container PK into the accommodation groove 12g, or deviation of the cartridge C in the container PK is large, there is a possibility that the radiation intensity cannot be measured accurately by moving the radiation intensity measuring means 30 as described above. However, in the radiation intensity measuring apparatus 1 of the present embodiment, since the radiation intensity is measured by moving the radiation intensity measuring means 30, it is possible to measure the radiation intensity accurately without necessity of setting the holding plate 12 and the container PK again by provision of a function of compensating the positional deviation based on the measurement result of the radiation intensity. Thus it is possible to reduce the time required for setting the holding plate 12 and the container PK again, and to suppress the radiation exposure to the operator.

For example, when the measured radiation intensity is generally low for all the radiation sources S in the cartridge C, a positional deviation in the x direction can occur. In such a case, by slightly shifting the position of the radiation intensity measuring means 30 in the measurement standby state in the x direction from the normal position in the measurement standby state, it is possible to accurately measure the radiation intensity. That is, it is possible to accurately measure the radiation intensity without conducting the operation of setting the holding plate 12 and the container PK again.

(Improvement in Measurement Accuracy by x-Directional Movement)

When the x-directional positions of the radiation sources S are misaligned from each other in the seed cartridge SC, after movement of a certain degree in the y direction, the movement in the y direction is temporarily stopped, and then reciprocal movement in the x direction may be effected. In this manner, it is possible to accurately measure the radiation intensity of each radiation source S even if the positions in the x direction of the radiation sources S are misaligned each other.

As described above, in the measurement standby state, the radiation intensity measuring means 30 is moved by the x-direction moving mechanism 22 to the position where the plane dividing the slit 35h into two halves in its axial direction contains the axial direction AL of one accommodation groove 12g, and then the radiation intensity measuring means 30 is moved in the y direction. Therefore, when such a state is established that all of the line dividing the radiation source S into two halves in its axial direction, the axial direction AL of the accommodation groove 12g, and the plane dividing the slit 35h into two halves in its axial direction coincide with each other (ideal position), the radiation irradiated from the radiation source S can be measured most efficiently by the radiation intensity measuring means 30. However, actually it is often the case that the position of the radiation source S is slightly deviated in the axial direction (namely, x direction) of the radiation source S with respect to the ideal position (see FIG. 15(A)). In this case, the amount of the radiation cut by the radiation emitting part 12s and the slit 35h increases compared with the case where the radiation sources S are arranged in the ideal position, and the detected radiation intensity can be slightly smaller.

In such a case, as described above, the radiation intensity measuring means 30 is moved in such a manner that after movement of a certain amount in the y direction, the movement in the y direction is temporarily stopped, and then the radiation intensity measuring means 30 is reciprocally moved in the x direction (see FIG. 15(B)). Then, even at the same y-direction position, the intensity of the radiation detected by the detecting part 31a of the sensor 31 changes, and the intensity peaks at a certain position. Then by calculating the radiation intensity of the radiation source S based on the intensity of the radiation at the position where the intensity peaks, the calculated radiation intensity is less different from the value of the radiation intensity in the case of measurement in the ideal position. That is, it is possible to accurately measure the intensity of the radiation of the radiation source S.

For example, when the positions in the x axial direction of the radiation sources a to c are misaligned as illustrated in FIG. 15(A), the intensities of the radiation sources a to c obtained by reciprocally moving the radiation intensity measuring means 30 in the x direction (see FIG. 15(B)) are as shown in FIG. 15(C).

That is, in the state that the cartridge C is accommodated in the accommodation groove 12g, when the cartridge C is positioned so that the line dividing the axial direction into two halves coincides with the axial direction A1 of the accommodation groove 12g as in the radiation source c, the radiation intensity shows the variation in which the radiation intensity peaks (for example, the curve of c in FIG. 15(C)) when the radiation intensity measuring means 30 is positioned at the position where the plane dividing the slit 35h into two halves in its axial direction coincides with the axial direction AL (corresponding to the position of 30c in FIG. 15(B), and the position of P in FIG. 15(C), for example).

On the other hand, if the line dividing the axial direction into two halves is deviated leftward with respect to the axial direction AL of the accommodation groove 12g as in the radiation source a, the radiation intensity shows the variation in which the radiation intensity peaks (for example, the curve of a in FIG. 15(C)) when the radiation intensity measuring means 30 is positioned at the position where the plane dividing the slit 35h into two halves in its axial direction is deviated leftward with respect to the axial direction AL (for example, the position of 30a in FIG. 15(B)).

On the contrary, if the line dividing the axial direction into two halves is deviated rightward with respect to the axial direction AL of the accommodation groove 12g as in the radiation source c, the radiation intensity shows the variation in which the radiation intensity peaks (for example, the curve of b in FIG. 15(C)) when the radiation intensity measuring means 30 is positioned at the position where the plane dividing the slit 35h into two halves in its axial direction is deviated leftward with respect to the axial direction AL (for example, the position of 30b in FIG. 15(B)).

Figure 15:
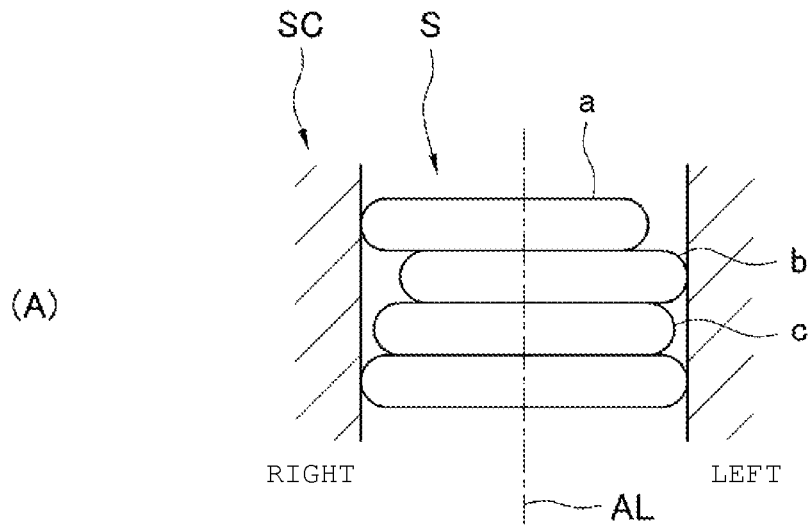
FIG. 15(A) is a schematic explanatory view in the state that radiation sources S are accommodated at axially displaced positions in a seed cartridge SC.
FIG. 15(B) is a schematic explanatory view when the radiation intensity is measured by moving a radiation intensity measuring means 30 in the state of (A)
FIG. 15(C) is a view exemplarily showing the measurement results of the radiation sources a to c in (A) when the radiation intensity is measured by the method of (B). The moving amount of the radiation intensity measuring means 30 in (B) is illustrated in the state that it is extremely moved for easy understanding of the operation, and is not necessarily coincident with the actual movement.
Figure 15:
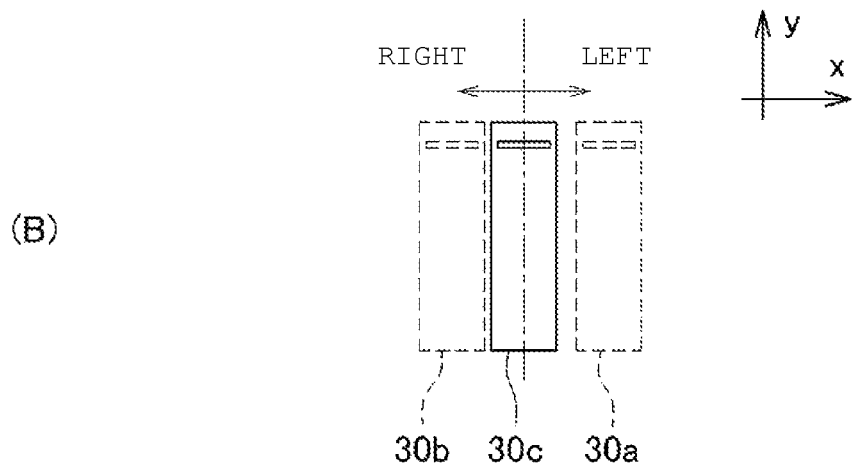
Figure 15:
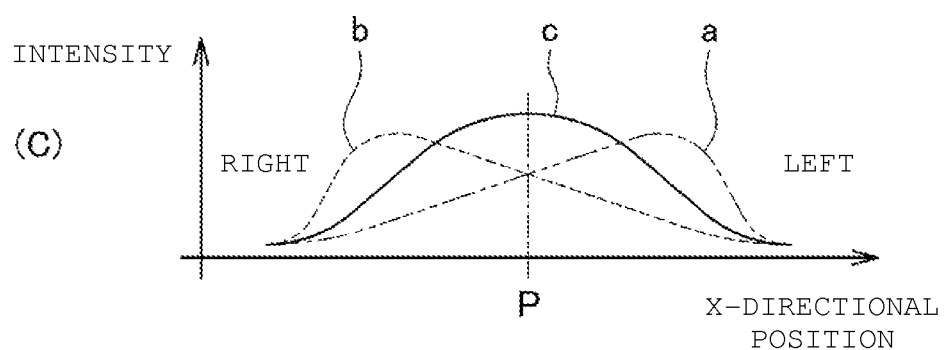

In FIG. 15, rightward and leftward mean the directions of right and left in a plan view (see FIG. 1).

The timing of reciprocally moving the radiation intensity measuring means 30 in the x direction is not particularly limited. For example, the radiation intensity measuring means 30 may be moved in such a manner that after movement of a certain amount in the y direction, the radiation intensity measuring means 30 is returned to the position where the peak value is detected, and the radiation intensity measuring means 30 is reciprocally moved in the x direction at that position. In this case, at the current position of the radiation source S, variation of the radiation intensity in the x direction can be confirmed at the position where the intensity of the radiation detected by the detecting part 31a of the sensor 31 peaks in the y direction. That is, since the radiation intensity of the radiation source S is measured at the position where the radiation intensity of the radiation source S passing through the radiation emitting part 12s and the slit 35h can be detected maximally at the current position of the radiation source S, it is possible to elevate the measurement accuracy of the radiation intensity of the radiation source S.

Further, regardless of whether a peak value is detected at the position, the radiation intensity measuring means 30 may be reciprocally moved in the x direction at the position reached by movement of a certain amount in the y direction. Also in this case, it is possible to grasp the position where the radiation intensity can be detected maximally in the x direction. Therefore, by correcting the radiation intensity of the radiation source S based on the difference between the position and the position where the plane dividing the slit 35h into two halves in its axial direction contains the axial direction AL of one accommodation groove 12g, it is possible to improve the accuracy of estimating the radiation source S.

Further, the radiation intensity measuring means 30 may be reciprocally moved in the x direction while it is moved in the y direction. Also in this case, by increasing the speed of the reciprocal movement in the x direction while decreasing the movement speed in the y direction to some extent, variation in the radiation intensity in the y direction and the variation in the radiation intensity in the x direction can be measured, and the radiation intensity of the radiation source S can be corrected depending on the measurement results.

(Calibration Part 40)

Regarding the radiation intensity of each radiation source S, it is possible to grasp whether each radiation source S is good or defective by relatively comparing respective peak values of the radiation source S in the variation curves of radiation intensity if their absolute values are not required.

On the other hand, in the case of grasping the absolute value of the radiation intensity of each radiation source S, it is desired to measure the variation curve of the radiation intensity for the cartridge C in which a reference radiation source having a reference radiation intensity is packed, prior to conducting measurement of the cartridge C to be measured. This makes it possible to grasp the absolute value of the radiation intensity of each radiation source S packed in the cartridge C to be measured from the measurement value (peak value) of the cartridge C to be measured, based on the peak value of the reference radiation source.

Particularly, in the case of sequentially measuring the multiple cartridges C accommodated in respective accommodation grooves 12g of the holding plate 12, the reference radiation source may be measured as is appropriate. For example, the reference radiation source may be measured every time before measuring the cartridge C. Also, the reference radiation source may be measured once before measuring the multiple cartridges C of each holding plate 12. That is, the reference radiation source may be measured directly after replacing the holding plate 12, and thereafter the multiple cartridges C may be successively measured.

By automating the measurement of the reference radiation source, it is possible to conduct measurement rapidly while keeping the measurement accuracy. For example, by designing the radiation intensity measuring means 30 to have the following structure, and providing the calibration part 40, it is possible to automate the measurement of the reference radiation source.

As illustrated in FIG. 4, in the shielding member 35 of the radiation intensity measuring means 30, the slit 35h is formed in its distal end part. A proximal end of the shielding member 35 is connected to the connecting part 32b of the sensor holding part 32 in a swingable manner so that its distal end part swings parallel with the opposed face 12a of the holding plate 12. Concretely, the shielding member 35 is provided movably between a measurement position where its distal end part is positioned above the detecting part 31a of the sensor 31 (see FIG. 6(A)), and a calibration position where its distal end part is moved from the detecting part 31a of the sensor 31 (see FIG. 6(B)). In other words, when the distal end part of the shielding member 35 is positioned in the measurement position, the detecting part 31a of the sensor 31 is covered with the distal end, and when the distal end of the shielding member 35 is positioned in the calibration position, the detecting part 31a of the sensor 31 is exposed.

In addition, the connecting part 32b of the sensor holding part 32 is provided with an urging means 36 for urging the distal end part of the shielding member 35 toward the measurement position from the calibration position. The urging means 36 also has a function of allowing the distal end part to swing to the measurement position when force is applied to the shielding member 35 in the direction of swinging the distal end part from the measurement position to the calibration position. And the connecting part 32b of the sensor holding part 32 is provided with a stopper 36a that comes into contact with the shielding member 35 when the distal end part of the shielding member 35 is positioned in the measurement position. That is, swinging of the shielding member 35 is restricted by the stopper 36a so that its distal end part cannot swing beyond the measurement position. Therefore, since the distal end part of the shielding member 35 is usually pushed against the stopper 36a by the urging means 36, it is possible to keep the distal end part of the shielding member 35 positioned in the measurement position. For example, when a spring is used as the urging means 36, the aforementioned function can be exerted.

Figure 5:
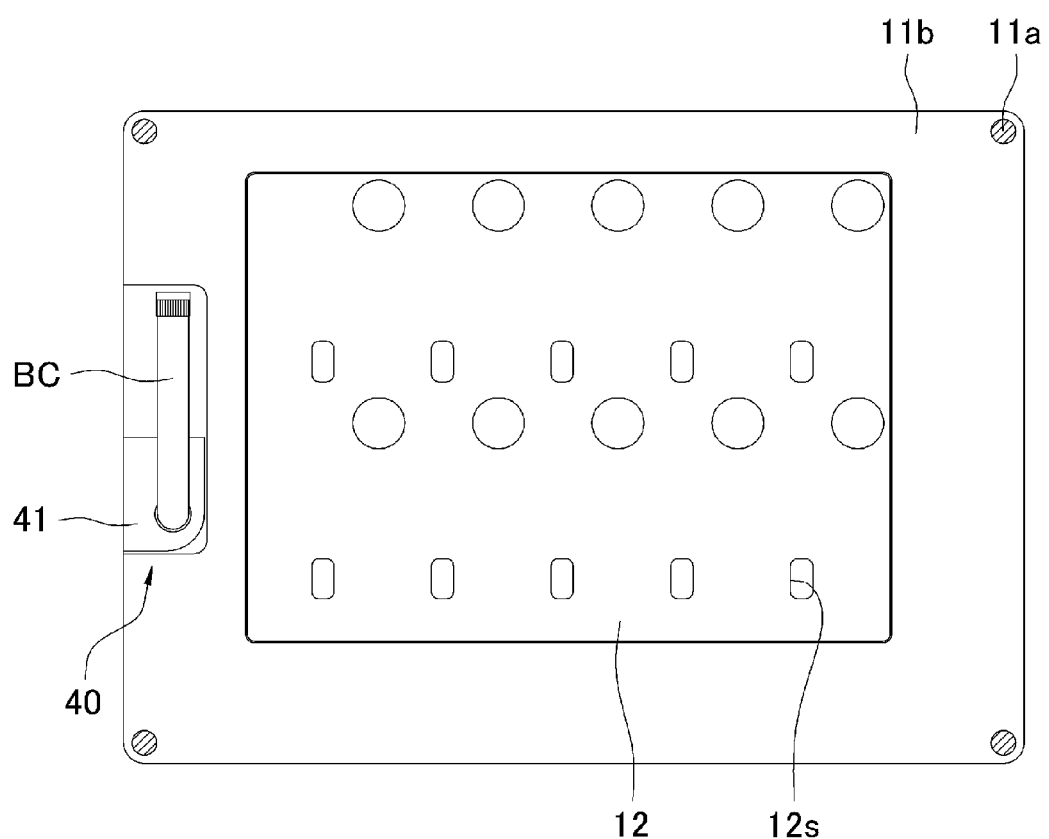
FIG. 5 is an arrow view along the line V in FIG. 3.

As illustrated in FIG. 5, on the back face of the holding part 11b of the frame part 11 of the holding means 10, the calibration part 40 is provided. The calibration part 40 is provided with a projecting part 41 projecting slightly on the side of the base 2 from the back face of the holding part 11b. The projecting part 41 is formed so that the distance from its surface on the side of the base 2 to the surface of the shielding member 35 of the radiation intensity measuring means 30 (face on the side of the holding plate 20) is shorter than the distance from the opposed face 12*a* of the holding plate 12 to the surface of the shielding member 35.

Further, on the surface on the side of the base 2 of the projecting part 41, a reference cartridge BC in which the reference radiation source is packed is disposed. The reference cartridge BC is held by the projecting part 41 so that the axial direction of the reference radiation source is parallel with the x direction. In other words, the reference cartridge BC is held by the projecting part 41 so that the axial direction of the reference radiation source is orthogonal to the y direction.

Figure 6:
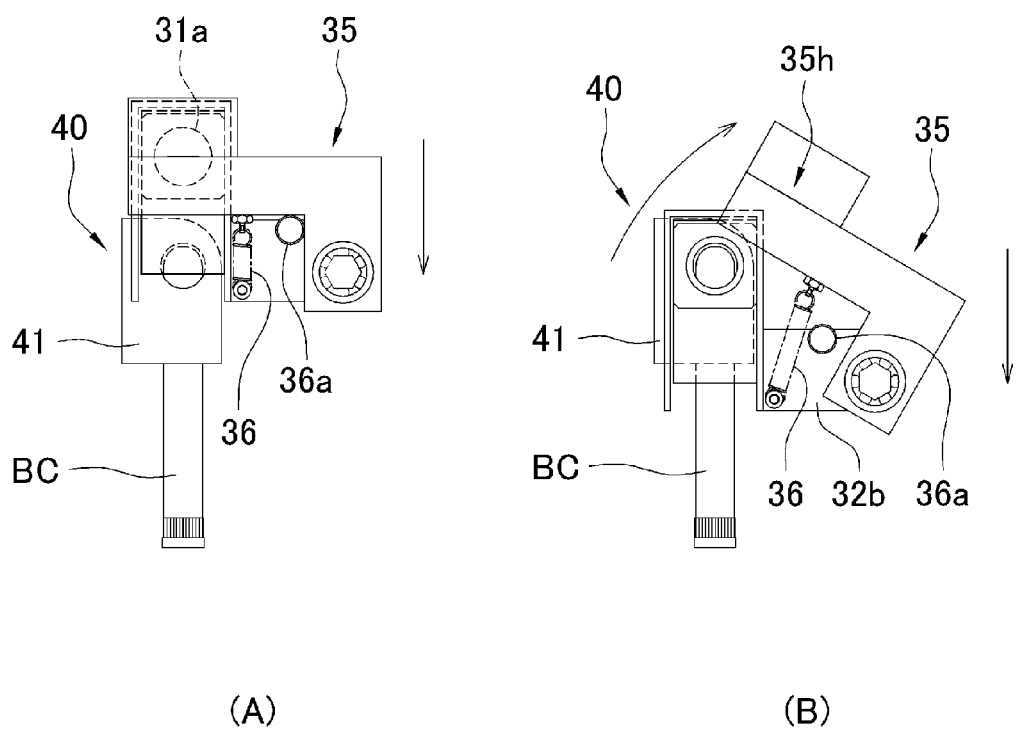
FIG. 6(A) is a schematic explanatory view in the state that a shielding member 32 is close to a calibration part 40.
FIG. 6(B) is a schematic illustrative view in the state that the shielding member 32 is positioned at a calibration position by a shielding member moving mechanism 45 of the calibration part 40.

Since the structure as described above is employed, as the radiation intensity measuring means 30 is moved toward the projecting part 41 from the y direction by the moving mechanism 20, the distal end part of the shielding member 35 comes into contact with the projecting part 41 (FIG. 6(A)). As the radiation intensity measuring means 30 is further moved in the y direction (the direction of the arrow in FIG. 6) from that state, a force is applied to the distal end part of the shielding member 35 in the direction of swinging from the measurement position to the calibration position. As a result, the distal end part of the shielding member 35 swings from the measurement position toward the calibration position against the urging force of the urging means 36. On the other hand, the sensor 31 moves below the projecting part 41.

Further, as the radiation intensity measuring means 30 is moved in the y direction, the distal end part moves from above the detecting part 31*a* of the sensor 31, and the detecting part 31*a* of the sensor 31 is completely exposed (FIG. 6(B)). Since the exposed detecting part 31*a* of the sensor 31 moves to the position facing with the reference radiation source of the reference cartridge BC, the detecting part 31*a* is directly irradiated with the radiation emitted from the reference radiation source.

Since the aforementioned configuration is employed, by moving the radiation intensity measuring means 30 from the y direction toward the projecting part 41 by the moving mechanism 20, it is possible to measure the intensity of the radiation emitted from the reference radiation source by the detecting part 31*a* of the sensor 31. Therefore, by conducting calibration of the sensor with reference to the measurement result, it is possible to keep the accuracy of estimating the radioactivity of the radiation source S high, based on the measurement result of the radiation intensity of the radiation source S of each cartridge C. In particular, by conducting calibration of the sensor 31 by the calibration part 40 every time before measuring each cartridge C, it is possible to keep the accuracy of estimating the radioactivity of the radiation source S of each cartridge C high.

In addition, only by moving the radiation intensity measuring means 30 from the y direction toward the projecting part 41 by the moving means 20, it is possible to conduct the calibration of the sensor 31. That is, since calibration of the sensor 31 can be automatically conducted, the number of operating steps conducted by an operator remains unchanged even when the calibration operation is conducted. Therefore, it is possible to prevent increase in the amount of radiation exposed to the operator during the calibration operation.

(Regarding Holding Plate 12)

In the above example, while the description was made for the case where the cartridge C hermetically sealed in the container PK is accommodated in the holding plate 12, the cartridge C may be accommodated in the accommodation groove 12*g* of the holding plate 12 as it is. Also in such a case, the accommodation groove 12*g* may be formed so that the multiple radiation sources S packed in the seed cartridge SC of the cartridge C are parallel with the opposed face 12*a* of the holding plate 12, and the arrangement direction of the multiple radiation sources S coincides with the axial direction AL of the accommodation groove 12*g* when the cartridge C is put into the accommodation groove 12*g*.

(Holding Plate 12B for Rectangular Cartridge C2)

In the case of measuring the rectangular cartridge C2, the shape of the accommodation groove 12*g* is made into coincident with the shape of the rectangular cartridge C2. For example, the holding plate 12B may have the shape as illustrated in FIG. 14.

Figure 14:
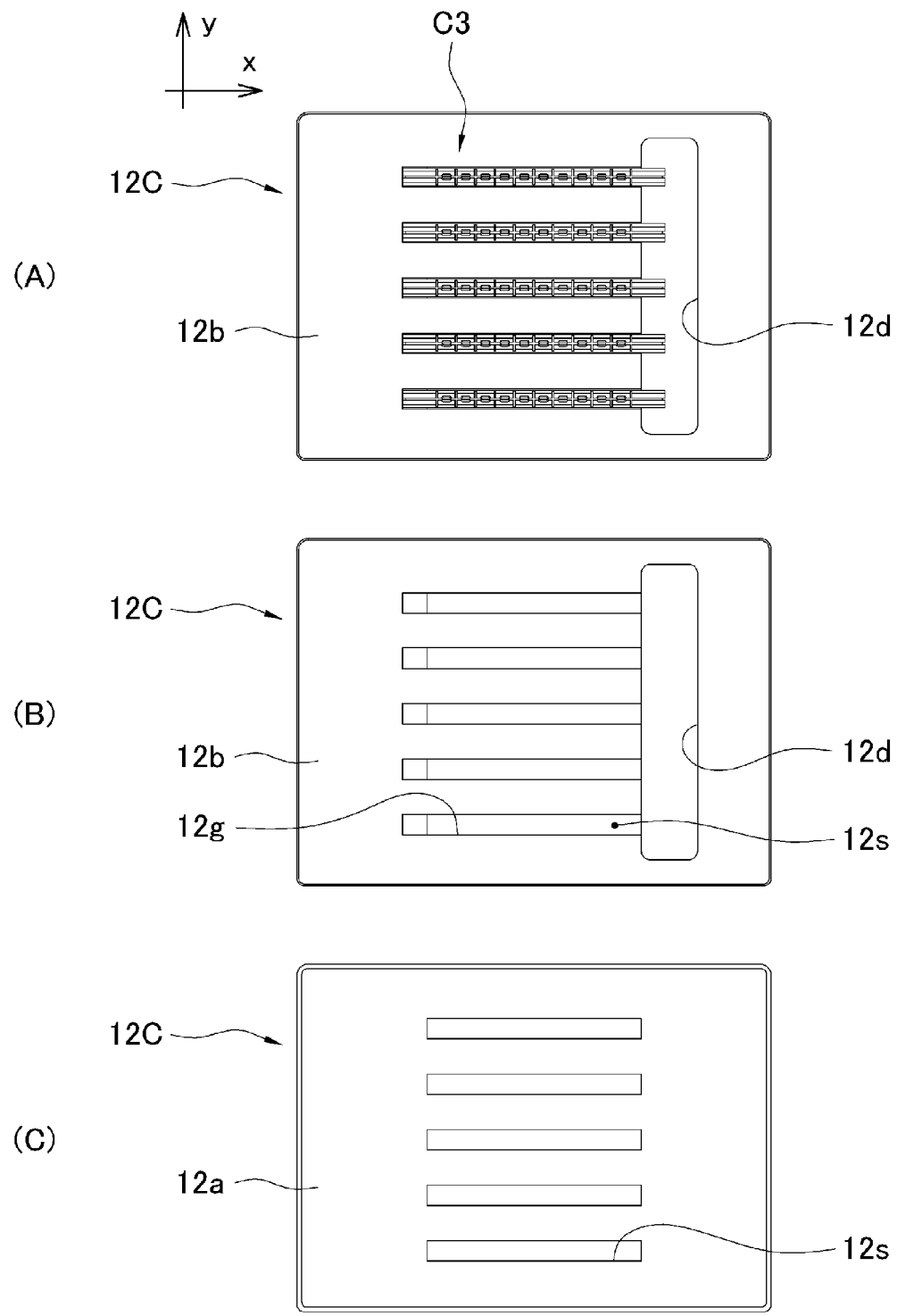

As illustrated in FIG. 14, an inner bottom face b of the accommodation groove 12*g* of the holding plate 12B is formed into a flat plane. As a result, when the rectangular cartridge C2 is accommodated in the accommodation groove 12*g*, the surface of the main body M of the rectangular cartridge C2 can be brought into surface contact with the inner bottom face b, with the result that it is possible to make the center axis of the multiple radiation sources S packed in the seed cartridge SC of the main body M parallel with the opposed face 12*a* of the holding plate 12. In addition, by forming the accommodation groove 12*g* to have substantially the same width as a width MD of the main body M of the rectangular cartridge C2 (see FIG. 11(B)), it is possible to accurately measure the radiation intensity of the multiple radiation sources S because the rectangular cartridge C2 will not rattle in the accommodation groove 12*g*.

In the rectangular cartridge C2 shown in FIG. 14, since an attachment is provided on the lateral side of the seed cartridge SC, it is desired to provide a groove 12*d* so that the attachment will not interfere with accommodation of the rectangular cartridge C2. The depth and width of the groove 12*d* are not particularly limited, and it is only required to be able to bring the surface of the main body M of the rectangular cartridge C2 into surface contact with the inner bottom face b.

By providing the grooves 12*d* in the manner of holding the accommodation groove 12*g* therebetween (in other words, on each end part of the accommodation groove 12*g*), it is possible to obtain the merit of making it easy to take out the rectangular cartridge C2 from the accommodation groove 12*g*.

(Holding Plate 12C for Shaft-Shaped Cartridge C3)

In the case of measuring the shaft-shaped cartridge C3 as described above, the shape of the accommodation groove 12*g* in the holding plate 12C may be made into coincident with the shape of the shaft-shaped cartridge C3.

For example, as illustrated in FIG. 14, unlike the cases of the holding plates 12, 12B, the holding plate 12C for shaft-shaped cartridge C3 is formed with the accommodation groove 12*g* so that the axial direction is parallel with the x direction when the holding plate 12C is attached to the holding part 11*b* of the frame part 11. The accommodation groove 12*g* supports both ends of the shaft-shaped cartridge C3 at its both end parts. The accommodation groove 12*g* is formed with a slit-like radiation emitting part 12*s* penetrating the accommodation groove 12*g* and the opposed face 12*a* between its both end parts. In the case of the holding plate 12C described above, it is possible to position the radiation source S accommodated in the strap member SB above the radiation emitting part 12*s* along the groove Mg of the main body M, or in other words, along the axial direction of the radiation emitting part 12*s* by positioning the shaft-shaped cartridge C3 in the accommodation groove 12*g*. That is, since the center axis of the shaft-shaped cartridge C3 (that is, the center axis of the radiation source S) and the center axis of the inner bottom face b are parallel with each other, the center axes of the multiple radiation sources S held by the shaft-shaped cartridge C3 can be brought into parallel with the opposed face 12a of the holding plate 12. Then, as described above, by moving the radiation intensity measuring means 30 along the y direction (that is, the direction orthogonal to the axial direction of each radiation source S) while the radiation intensity measuring means 30 is sequentially moved below each radiation source S in the cartridge C3 to be measured, it is possible to individually measure the intensity of the radiation emitted from each radiation source S.

Also, as illustrated in FIG. 14, by providing the groove 12d in one (or both) of end parts of the accommodation groove 12g in the holding plate 12C, it is possible to obtain a merit of making it easy to take out the shaft-shaped cartridge C3 from the accommodation groove 12g.

(Holding Plate for Connecting Cartridge)

Also, in the case of measuring the aforementioned connecting cartridge, the shape of the accommodation groove 12g may be made into coincident with the shape of the connecting cartridge. For example, the inner bottom face b of the accommodation groove 12g may be formed into a cylindrical shape, and the center axis of the inner bottom face b is made to be parallel with the opposed face 12a of the holding plate 12. As a result, when the connecting cartridge is accommodated in the accommodation groove 12g, the center axis of the connecting cartridge (center axis of the radiation source S) and the center axis of the inner bottom face b are parallel with each other, so that it is possible to make the center axes of the multiple radiation sources S held by the connecting cartridge into parallel with the opposed face 12a of the holding plate 12. In addition, by forming the cylindrical shape of the inner bottom face b of the accommodation groove 12g and its radius of curvature to have the same length as the radius of the outer diameter of the connecting cartridge, the connecting cartridge will not rattle in the accommodation groove 12g, with the result that it is possible to measure the radiation intensity of the multiple radiation sources S accurately.

When the shapes of the holding plates 12B, 12C for accommodating the rectangular cartridge C2 and the shaft-shaped cartridge C3, or the shape of the holding plate for accommodating the cartridge of other shape are made to be substantially equal to the shape of the aforementioned holding plate (the holding plate 12 for accommodating the container PK), it is possible to change the cartridge to be measured only by replacing the holding plate. That is, by preparing holding plates having different shapes of accommodation groove, it is possible to deal with multiple cartridges by one apparatus.

The holding plates 12B, 12C for accommodating the rectangular cartridge C2 and the shaft-shaped cartridge C3, and the holding plate for accommodating the cartridge of other shape are not limited to those accommodating multiple of the rectangular cartridges C2 or the like, but may be those accommodating only one rectangular cartridge C2 or the like. That is, it may have only one accommodation groove 12g. Also in this case, likewise the case where the holding plate 12 holds only one container PK as described above, it is possible to make the holding plate 12 compact, so that a merit of downsizing the apparatus is obtained.

(Regarding the Configuration in which Holding Plate 12 is not Provided)

In the above description, the case where the holding means 10 has the holding plate 12 is described. However, a groove having an equivalent structure as the accommodation groove 12g of the holding plate 12 may be formed in the holding part 11b of the frame part 11 without providing the holding plate 12.

For example, the case where 15 radiation sources S are accommodated in one cartridge C is considered. Since the number of radiation sources S to be used for one patient is normally about 50 to 150, it is possible to test every radiation source S to be used for one patient at one measurement by providing the grooves at ten positions. In the case of use in such a state, it is possible to measure the radiation intensity rapidly for every radiation source S required for the therapy without having the structure that enables holding plate 12 to be attached or detached to/from the holding part 11b. In this case, the plate having the same structure as the holding plate 12 may be directly fixed to the multiple leg parts 11a to give the holding part 11b. As a result, even in the case of measuring the cartridge C having a different shape (for example, the rectangular cartridge C2 or the shaft-shaped cartridge C3), it is possible to measure the radiation intensity of the radiation source S accommodated in the cartridge C having the different shape by replacing the plate having the same structure as the holding plate 12, and to facilitate the replacement of the plate.

INDUSTRIAL APPLICABILITY

The radiation intensity measuring apparatus for small sealed radiation sources for cancer therapy of the present invention is suited for measuring radiation intensity of small sealed radiation sources for use in small sealed radiation source therapy for prostate cancer.

DESCRIPTION OF REFERENCE SIGNS 1 radiation intensity measuring apparatus
1h measurement space
10 holding part
11 frame part
12 holding plate
12a opposed face
12g accommodation groove
12s radiation emitting part
20 moving mechanism
30 radiation intensity measuring means
31 sensor
31a detecting part
35 shielding member
35h slit
40 calibration part
C cartridge
SC seed cartridge

The invention claimed is:

1. A radiation intensity measuring apparatus for small sealed radiation sources for cancer therapy, in which multiple radiation sources are held in a cartridge, and radiation intensity of the multiple radiation sources is measured while they are held by the cartridge, the apparatus comprising:
   holding means capable of holding the cartridge;
   radiation intensity measuring means for measuring intensity of radiation emitted from the multiple radiation sources packed in the cartridge in the state that the cartridge is held by the holding means; and
   moving means for moving the radiation intensity measuring means toward or away from the holding means, the holding means including:
a radiation emitting part capable of emitting radiation emitted from the multiple radiation sources outside the holding means in the state that the cartridge is held by the holding means,
the radiation intensity measuring means including:
a sensor for measuring radiation intensity, and
a shielding member provided for restricting radiation irradiated to the sensor;
the shielding member being disposed to be positioned between the radiation emitting part of the holding means and the sensor in a measurement state where the radiation intensity measuring means is moved toward the radiation emitting part of the holding means,
the shielding member being formed with a slit that penetrates between a face positioned on the side of the radiation emitting part of the holding means and a face positioned on the side of the sensor in the measurement state,
the slit being formed so that width thereof is smaller than a wire diameter of the radiation source,
the moving means being configured to be able to relatively move the radiation intensity measuring means along the direction orthogonal to an axial direction of each radiation source held by the cartridge in the measurement state.

2. The radiation intensity measuring apparatus for small sealed radiation sources for cancer therapy according to claim 1, wherein
the moving means is controlled to move the radiation intensity measuring means also in an axial direction of the radiation source in relatively moving the radiation intensity measuring means along the direction orthogonal to the axial direction of the radiation source held by the cartridge in the measurement state.

3. The radiation intensity measuring apparatus for small sealed radiation sources for cancer therapy according to claim 1, wherein
the cartridge has a seed holding part in which the multiple radiation sources are packed so that the axial directions of the multiple radiation sources are substantially parallel with each other, and
the moving means is configured to be able to relatively move the radiation intensity measuring means along the direction in which the multiple radiation sources are arranged in the seed holding part of the cartridge in the measurement state.

4. The radiation intensity measuring apparatus for small sealed radiation sources for cancer therapy according to claim 1, wherein
the holding means is configured to be able to hold multiple cartridges, and has the multiple radiation emitting parts each corresponding to positions of the seed holding parts of the multiple cartridges in the state that the multiple cartridges are held.

5. The radiation intensity measuring apparatus for small sealed radiation sources for cancer therapy according to claim 1, wherein
the moving means is able to position the radiation intensity measuring means to give a state that an axial direction of the radiation source to be measured in the measurement state and an axial direction of the slit of the shielding member are parallel with each other, and move the radiation intensity measuring means while keeping the state.

6. The radiation intensity measuring apparatus for small sealed radiation sources for cancer therapy according to claim 1, wherein
the holding means has an opposed face situated on the side of the radiation intensity measuring means in the measurement state, and a supply face situated on the opposite side of the opposed face,
the supply face is formed with an accommodation groove recessed from the supply face to the opposed face, for accommodating the cartridge,
the accommodation groove is formed so that the axial directions of the multiple radiation sources are parallel with the opposed face when the cartridge is accommodated in the accommodation groove, and
the radiation emitting part is formed at positions corresponding to the positions where the multiple radiation sources are positioned when the cartridge is accommodated in the accommodation groove.

7. The radiation intensity measuring apparatus for small sealed radiation sources for cancer therapy according to claim 6, wherein the radiation emitting part is a through hole penetrating between an inner bottom face of the accommodation groove and the opposed face.

8. The radiation intensity measuring apparatus for small sealed radiation sources for cancer therapy according to claim 1, further comprising a base in which the moving means is provided, wherein
the holding means includes:
a holding plate for holding the cartridge, and
a frame part for positioning the holding plate apart from the base,
the radiation emitting part is provided at a position where radiation from the radiation source can be emitted into a space between the holding plate and the base in the holding plate, and
the radiation intensity measuring means is disposed to be able to move in the space between the holding plate and the base by the moving means.

9. The radiation intensity measuring apparatus for small sealed radiation sources for cancer therapy according to claim 8, wherein
the holding plate has a flat reference face on the side of the base, and holds the cartridge so that the axial directions of the multiple radiation sources are parallel with the reference face,
the radiation intensity measuring means is provided so that a shielding face situated on the side of the radiation emitting part of the holding means in the shielding member and the reference face are parallel with each other, and
the moving means moves the radiation intensity measuring means while keeping the shielding face and the reference face parallel with each other.

10. The radiation intensity measuring apparatus for small sealed radiation sources for cancer therapy according to claim 8, wherein the holding plate is provided detachably from the frame part.

11. The radiation intensity measuring apparatus for small sealed radiation sources for cancer therapy according to claim 1, further comprising:
a calibration part provided with a reference radiation source which is a reference of intensity of radiation emitted from the radiation source, wherein
the shielding member is provided so as to be movable between a measurement position where a detecting part of the sensor is covered, and a calibration position where the detecting part of the sensor is exposed, and the calibration part is provided with a shielding member moving mechanism for moving the shielding member to the calibration position while moving the radiation intensity measuring means to the position of the reference radiation source of the calibration part by the moving means.

* * * * *